US010537725B2

(12) United States Patent
Lewis, Jr. et al.

(10) Patent No.: US 10,537,725 B2
(45) Date of Patent: Jan. 21, 2020

(54) ULTRASOUND-ASSISTED CONVECTION ENHANCED DELIVERY OF COMPOUNDS IN VIVO WITH A TRANSDUCER CANNULA ASSEMBLY

(75) Inventors: George K. Lewis, Jr., Ithaca, NY (US); William L. Olbricht, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 675 days.

(21) Appl. No.: 13/582,663

(22) PCT Filed: Mar. 4, 2011

(86) PCT No.: PCT/US2011/027238
§ 371 (c)(1),
(2), (4) Date: Nov. 7, 2012

(87) PCT Pub. No.: WO2011/109735
PCT Pub. Date: Sep. 9, 2011

(65) Prior Publication Data
US 2013/0046230 A1 Feb. 21, 2013

Related U.S. Application Data

(60) Provisional application No. 61/311,064, filed on Mar. 5, 2010.

(51) Int. Cl.
*A61M 37/00* (2006.01)
(52) U.S. Cl.
CPC .......... *A61M 37/0092* (2013.01); *Y10T 29/42* (2015.01)
(58) Field of Classification Search
CPC ............................ A61M 37/0092; A61N 7/00
(Continued)

(56) References Cited

U.S. PATENT DOCUMENTS 5,190,046 A * 3/1993 Shturman ...................... 600/463
5,590,657 A * 1/1997 Cain et al. ..................... 600/439
(Continued)

FOREIGN PATENT DOCUMENTS

| RU | 2386111 C1 | 1/1986 | |
| WO | WO 9717105 A1 * | 5/1997 | ......... A61B 18/1477 |
| WO | WO2010006293 A3 | 1/2010 | |

OTHER PUBLICATIONS

Lewis, Olbricht, Design and characterization of a High power ultrasound driver with ultralow-output impedance, 2009, Review of Scientific Instruments, 80, pp. 114704-114704-8.*
(Continued)

*Primary Examiner* — Emily L Schmidt
(74) *Attorney, Agent, or Firm* — Heslin Rothenberg Farley & Mesiti P.C.; George Blasiak

(57) ABSTRACT

A method for convection-enhanced delivery (CED) of compounds and an apparatus for use with the method are provided. The apparatus, an ultrasound transducer cannula assembly (TCA) apparatus, can be used for the delivery of a compound to a target in the body such as a cells, tissue or organ in a healthy or diseased state. The ultrasound TCA apparatus comprises a transducer cannula assembly (TCA) and an ultrasound system to enhance penetration of molecules in the target. The ultrasound system may be portable and pocket-sized. The inclusion of ultrasound in the apparatus improves the distribution volume of material four to six times over a convection-enhanced delivery system without ultrasound. Since the targeting can be more focused, less compound is needed, thus lowering the potential for harmful effects to the host and host cells.

46 Claims, 14 Drawing Sheets

SCHEMATIC SHOWING INFUSION COORDINATES (β + 0 mm)

Figure 1A:
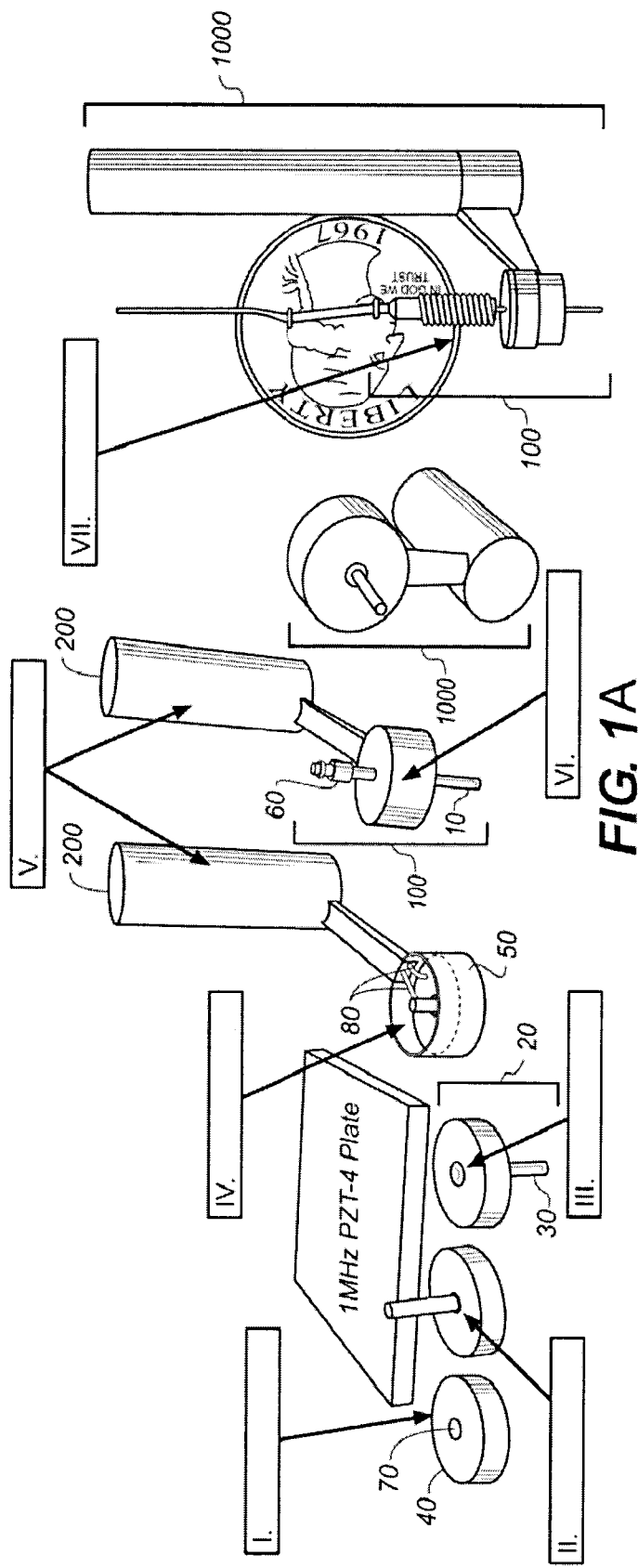

(58) Field of Classification Search
USPC .................................................. 604/20, 22
See application file for complete search history.

(56) References Cited

U.S. PATENT DOCUMENTS

| | | | |
|---|---|---|---|
| 5,620,479 A * | 4/1997 | Diederich | 601/3 |
| 5,624,396 A * | 4/1997 | McNamara | A61B 17/22 |
| | | | 604/264 |
| 6,176,842 B1 * | 1/2001 | Tachibana et al. | 604/22 |
| 6,224,566 B1 * | 5/2001 | Loeb | 604/22 |
| 2002/0055702 A1 * | 5/2002 | Atala | A61M 37/0092 |
| | | | 604/20 |
| 2002/0055731 A1 * | 5/2002 | Atala et al. | 604/522 |
| 2002/0099356 A1 * | 7/2002 | Unger et al. | 604/501 |
| 2002/0138036 A1 | 9/2002 | Babaev | |
| 2004/0073114 A1 | 4/2004 | Oliver et al. | |
| 2004/0186384 A1 * | 9/2004 | Babaev | A61M 3/0275 |
| | | | 600/489 |
| 2007/0016041 A1 * | 1/2007 | Nita | A61N 7/022 |
| | | | 600/439 |
| 2007/0055180 A1 * | 3/2007 | Deem et al. | 601/2 |

OTHER PUBLICATIONS

International Search Report for International Application No. PCT/US2011/027238, dated Nov. 15, 2011.
Bobo, RH, Laske, DW, Akbasak, A, Morrison, PF, Dedrick, RL, Oldfield, EH. Convection-enhanced delivery of macromolecules in the brain. Proc. Natl. Acad. Sci. U SA 91, 2076-2080 (1994).
Morrison, PF, Chen, My, Chadwick, RS, Lonser, RR, Oldfield, EH. Focal delivery during direct infusion to brain: role of flow rate, catheter diameter, and tissue mechanics, Am. J. Physiol. Regul. Integr. Comp. Physiol. 277 R1218—R1229.1580-1596 (1999).
Murad, GJ, Walbridge, S, Morrison, PF, et al. Real-time, image-guided, convection-enhanced delivery of interleukin 13 bound to pseudomonas exotoxin. Clin Cancer Res. 12, 3145-3151 (2006).
Yang, W, Barth, RF, Adams, DM, Ciesielski, MJ, Fenstermaker, RA, Shukla, S, Tjarks, W, Cligiuri, MA. Convection-enhanced delivery of boronated epidermal growth factor for molecular targeting of egf receptorpositive gliomas. Cancer Res. 62, 6552-6558 (2002).
Yamashita, Y, Krauze, MT, Kawaguchi, T, Noble, CO, Drummond, DC, Park, JW, Bankiewicz, KS. Convection-enhanced delivery of a topoisomerase I inhibitor (nanoliposomal topotecan) and a topoisomerase I inhibitor (pegylated liposomal doxorubicin) in intracranial brain tumor xenografts. Neuro Oncol. 9, 20-28 (2007).
Noble, CO, Krauze, MT, Drummond, DC, Yamashita, Y, Saito, R, Berger, MS, Kirpotin, DB, Bankiewicz, KS. Novel nanoliposomal CPT-11 infused by convection-enhanced delivery in intracranial tumors: pharmacology and efficacy. Cancer Res. 66, 2801-2806 (2006).
Krauze, MT, Forsayeth, J, Park, JW, Bankiewicz, KS. Real-time imaging and quantification of brain delivery of liposomes. Pharm Res. 23, 2493-2504 (2006).
Reddy, ST, Berk, DA, Jain, RK, Swartz, MA. A sensitive in vivo model for quantifying interstitial convective transport of injected macromolecules and nanopartivles. J Appl Physiol. 101, 1162-1169 (2006).
Neeves, KB, Sawyer, AJ, Foley, CP, Saltzman, WM, Olbricht, WL. Dilation and degradation of the brain extracellular matrix enhances penetration of infused polymer nanoparticles. Brain Res. 1180, 121-132 (2007).
Ren, H, Boulikas, T, Soling, A, Warnke, PC, Rainov, NG. Immunogene therapy of recurrent glioblastoma multiforme with a liposomally encapsulated replication-incompetent semliki forest virus vector carrying the human interleukin-12 gene a phase i/ii clinical protocal. J. Neuro-oncol. 64, 147-154(2003).
Sampson, JH, Akabani, G, Archer, GE, Bigner, DD, Berger, MS, Friedman, AH, Friedman, HS, Herndon II, J, Kunwar, S, Marcus, S, McLendon, RE, Paolino, A, Penne, K, Provenzale, J, Quinn, J, Reardon, DA, Rich, J, Stenzel, T, Tourt-Uhlig, S, Wikstrand, C, Wong, T, Williams, R, Yuan, F, Zalutsky, Mr, Pastan. (.Progress report of a phase i study of the intracerebral microinfusion of a recombinant chimeric protein composed of transforming growth factor (tgf)-a and a mutated form of the Pseudomonas exotoxin termed pe-38 (tp-38) for the treatment of malignant brain tumors. J. Neuro-oncol. 65, 37-35 (2003).
Kunwar S, Prados MD, Chang SM, Berger, MS, Laff, FF. Direct intracerebral delivery of cintredekin besudotox (1L,13-PE38QQR) in recurrent malignant glioma: a report by the Cintredekin Besudotox Intraparenchymal Study Group. J Clin Oncol. 25, 837-844 (2007).
Raghavan R, Brady MD, Rodriguez-Ponce MI, Hartlep A, Pedain C, Sampson JH. Convection-enhanced delivery of therapeutics for brain disease, and its optimization. Neurosurg Focus. 20, El 2 (2006).
Hall, WA, Sherr, GT. Convection-enhanced delivery: targeted toxin treatment of malignant glioma. Neurosurg Focus. 20, El 0 (2006).
Shimamura, T, Husain SR, Puri, RK. The IL-4 and IL-13 pseudomonas exotoxins: new hope for brain tumor therapy. Neurosurg Focus. 20, E11 (2006).
Vogelbaum MA. Convection enhanced delivery for treating brain tumors and selected neurological disorders: symposium review. J Neurooncol. 83, 97-109 (2007).
Sarntinoranont, M, Chen, X, Zhao, J, Mareci, TH. Computational model of interstitial transport in the spinal cord using diffusion tensor imaging. Ann, Biomed. Eng. 34, 1304-1321 (2006).
Mitragotri, S, Blankschtein, D, Langer, R. Ultrasound-mediated transdermal protein delivery. Science. 269, 850-853 (1995).
Park, EJ, Werner, J, Smith, NB. Ultrasound mediated transdermal insulin delivery in pigs using a lightweight transducer. Pharm Res. 24, 1396-1401 (2007).
Guzman, HR, Nguyen, DX, McNamara, AJ, Prausnitz, Mr. Equilibrium loading of cells with macromolecules by ultrasound: effects of molecular size and acoustic energy. J. Pharm. Sci. 91-1693-1701 (2002).
Keyhani, K, Guzman, HR, Parsons, A, Lewis, TN, Prausnitz, MR. Intracellular drug delivery using lowfrequency ultrasound: quantification of molecular uptake and cell viability. Pharm. Res. 18, 15141520 (2001).
Sundaram, J, Mellein, BR, Mitragotri, S. An experimental and theoretical analysis of ultrasound- induced permeabilization of cell membranes. Biophys. J. 84, 3087-3101 (2003).
Hynynen K, Clement G. Clinical applications of focused ultrasound—the brain. Int. J. Of Hyperther.23, 193-202 (2007).
Hynynen K.Ultrasound for drug and gene delivery to the brain. Adv. Drug Deliv. Rev. 60, 1209-1217 (2008).
Hynynen, K, McDannold, N, Vykhodtseva, N, Raymond, S, Weissleder, R, Jolesz, FA, Sheikov, N. Focal disruption of the blood-brain barrier due to 260-kHz ultrasound bursts: A method for molecular imaging and targeted drug delivery, J. Neurosurg. 105, 445-454 (2006).
Hynynen, K, McDannold, N, Sheikov, NA, Jolesz, FA, Vykhodtseva, N. Local and reversible bloodbrain barrier disruption by noninvasive focused ultrasound at frequencies suitable for trans-skull sonications. Neuroimage. 24, 12-20 (2005).
Denk, W, Strickler, JH, Webb, WW. Two-photon laser scanning fluorescence microscopy. Science 248, 73-76 (1990).
[Squirrell, JM, Wokosin, DL, White, JG, Bavister, BD. Long-term two-photon fluorescence imaging of mammalian embryos without compromising viability. Nat Biotechnol. 17, 763-7 (1999).
Dombeck, DA, Kasischke, KA, Vishwasrao, HD, Ingelsson, M, Hyman BT, and Webb, WW. Uniform polarity microtubule assemblies imaged in native brain tissue by second-harmonic generation microscopy . . . Proc. Natl. Acad. Sci. 100, 7081-7086 (2003).
Levene, MJ, Dombeck, DA, Molloy, RP, Kasischke, R, Williams, Zipfel, WR, and Webb, WW. In vivo multiphoton microscopy of deep brain tissue. J. Neurophys. 91, 1908-1912 (2004).
Henderson, P, Lewis Jr., GK, Olbricht, WL, Spector, J, A portable high intensity focused ultrasound device for the non invasive treatment of varicose veins, J. Vas. Surg. In press (2009).
Foley, CP, Nishimura, N, Neeves, KB, Schaffer, CB, and Olbricht, WL. Flexible microfluidic devices supported by biodegradable insertion scaffolds for convection-enhanced neural drug delivery. Biomed. Microdevices. 11, 1572-8781 (2009).

(56) References Cited

OTHER PUBLICATIONS

Zipfel, WR, Williams, RM, Christie, R, Nikitin, AY, Hyman, BT, and Web, WW. Live tissue intrinsic emission microscopy using multiphoton-excited native fluorescence and second harmonic generation. Proc. Nat. Acad. Sci. 100, 7075-7080 (2003).
Ohl CD, Arora M, !kink R. Sonoporation from jetting cavitation bubbles. Biophys J. 91, 4285-4295 (2006).
Smith, NB, Lee, S, Shang, K. Ultrasound—mediated transdermal in vivo transport of insulin with low- profile cymbal arrays. J. ultra. Med. Bio.29, 1205-1210 (2003).
V. Frenkel, et al. "*Pulsed-High Intensity Focused Ultrasound Enhanced tPA Mediated Thrombolysis in a Novel in Vivo Clot Model, a Pilot Study*" Radiology. 239, 86-93, (2006).
V. Frenkel, et al. "*Ultrasound-Facilitated Transport of Silver Chloride (AgCl) Particles in Fish Skin*" J. Control Release, 68, 251-261 (2000).
A. Van Wamel, et al. "*Vibrating Microbubbles Poking Individual Cells: Drug Transfer into Cells via Sonoporation*"J. Control Release 112, 149-155 (2006).
M. Chen, et al. "*Variables Affecting Convection-Enhanced Delivery to the Striatum: a Systematic Examination of Rate of Infusion, Cannula Size, Infusate, Concentration, and Tissue-Cannula Sealing Time*" J. Neurosurg. 90, 315-320 (1999).
N.G. Rainov, et al. "*Novel Therapies for Malignant Gliomas: A Local Affair?*" Neurosurg Focus, 20, E9 (2006).
R.R. Lonser, et al. "*Convection-Enhanced Selective Excitotoxic Ablation of the Neurons of the Globus Pallidus Internus for Treatment of Parkinsonism in Nonhuman Primates*" J. Neurosurg. 91, pp. 294- 302, 1999.
D. Groothuis et al. "*Comparison of 14 C-Sucrose Delivery to the Brain by Intravenous, Intraventricular, and Convection-Enhanced Intracerebral Infusion*" J. Neurosurg, 90, pp. 321-331 (1999).
D. Lieberman et al. "*Convection-Enhanced Distribution of Large Molecules in Gray Matter during interstitial Drug Infusion*" J. Neurosurg, 82, pp. 1021-1029 (1995).
Laske et al. "*Chronic Interstitial Infusion of Protein to Primate Brain: Determination of Drug Distribution and Clearance with Single-Photon Emission Computerized Tomography Imaging*" J. Neurosurg, 87, pp. 586-594 (1997).
R. Lonser et al. "*Successful and Safe Perfusion of the Primate Brainstem: in Vivo Magnetic Resonance Imaging of Macromolecular Distribution During Infusion*" J. Neurosurg 97, pp. 905-913 (2002).
J. Hamilton et al. "*Heparin Coinfusion During convection-Enhanced Delivery (CED) Increases the Distribution of the Glial-Derived Neurotrophic Factor (GDNF) Ligand Family in Rat Striatum and Enhances the Pharmacological Activity of Neurturin*" Experimental Neurology, 168, pp. 155-161, 2001.
D. Groothuis et al. "*Comparison of Cytosine Arabinoside Delivery to Rat Brain by Intravenous, Intrathecal, Intraventricular, and Intraparenchymal Routes of Administration*" Brain Research, 856, pp. 281-290, 2000.
J.A. Mackay et al. "*Distribution in Brain of Liposomes After Convection Enhanced Delivery- Modulation by Particle Charge, Particle Diameter, and Presence of Steric Coating*" Brain Research, 1035, pp. 139-153 (2005).
M. Chen et al. "*Surface Properties, More than Size, Limiting Convective Distribution of Virus-Sized Particles, and Viruses in the Central Nervous System*" J. Neurosurg, 103, pp. 311-319, 2005.
Y. Mardor et al. "*Monitoring Response to Convection-Enhanced Taxol Delivery in Brain Tumor Patients Using Diffusion-Weighted Magnetic Resonance Imaging*" Cancer Research. 61, pp. 4971-49736 (2001).
Z. Lidar et al. "*Convection-Enhanced Delivery of Paclitaxel for the Treatment of Recurrent Malignant Glioma: a Phase Ix Clinical Study*" J. Neurosurg, 100, pp. 472-479, 2004.
F. Weber et al. Safety Tolerability, and Tumor Response of IL4-Psudomonas Exotoxin (NBI-3 OW) in Patients with Recurrent Malignant Glioma) Journal of Neuro-Oncology, 64, pp. 125-137, 2001.

J. Sampson et al. "Intracerebral Infusate Distribution by Convection-Enhanced Delivery in Humans with Malignant Gliomas: Descriptive Effects of Target Anatomy and Catheter Positioning" Neuosurgery, 60, ONS89-98, Discussion ONS98-9 (2007).
Lopez et al. "*Convection-Enhanced Delivery in the Treatment of Malignant Glioma*" Neurology Research 28, pp. 542-548 (2006).
W. Vandergrift et al. "*Convection-Enhanced Delivery of Immunotoxins and Radioisotopes for Treatment of Malignant Gliomas*" Neurosurg Focus 20, E13, 2006.
G. Ter Haar "*Therapeutic Applications of Ultrasound*" Progress in Biophysics and Molecular Biology 93, pp. 111-129 (2007).
Benson et al. "*Proteins and Peptides: Strategies for Delivery to an Across the Skin*" J. Pharm. Sci., published online: www.interscience.wiley.com DOI 10.1002/jps.21277 (2008).
C.C. Coussios et al. "*Applications of Acoustics and Cavitation to Noninvasive Therapy and Drug Delivery*" Annual Review of Fluid Machanics, fluid.annualreview.org, DOI 10.1146/armurev.fluid.40.111406.102116.
RV Siioiiet et al. "*Echocardiographic Destruction of Albumin Microbubbles Directs Gene Delivery to Myocardium*" Circulation 10101, 2554-6 (2000).
Sheikov et al. "*Cellular Mechanisms of the Blood-Brain Barrier Opening Induced by Ultrasound in Presence of Microbubbles*" Ultrasound Med. Biol. 30, 979-89, 2004.
Koike et al. "*An Efficient Gene Transfer Method Mediated by Ultrasound and Microbubbles into the Kidney*" the Journal of Gene Medicine 7, 108-16, 2005.
J.T. Patrick et al. "*Ultrasound and the Blood-Brain Barrier*" Adv. Exp. Med. Biol. 267, 369-81, 1990.
G. Lewis et al. "*A Phantom Feasibility Study of Acoustic Enhanced Drug Diffusion in Neurological Tissue*" IEEE Lisa, 67-70, 2007.
G. Lewis et al. "*Acoustic Targeted Drug Delivery in Neurological Tissue*" J. Acoustical Soc. Am. 122, 3007 (2007).
Dayton et al. "*Acoustic Radiation in Vivo: A Mechanism to Assist Targeting of Microbubbles*" Ultrasound, Med. Biol. 25, pp. 1195-1201, 1999.
Vykhodtseva et al. "*Histologic Effects of High Intensity Pulsed Ultrasound Exposure with Subharmonic Emission in Rabbit Brain in Vivo*" Ultrasound Med Biol. 21, pp. 969-979, 1995.
Mesiwala et al. "*High-Intensity Focused Ultrasound Selectively Disrupts the Blood-Brain Barrier in Vivo*" Ultrasound, Med. Biol. vol. 28, No. 3, pp. 389-400, 2002.
M. Reinhard et al. "*Blood-Brain Barrier Disruption by Low-Frequency Ultrasound*" Stroke 37, 1546-1548. 2006.
N. Mcdannold et al. "*MRI-Guided Targeted Blood-Brain Barrier Disruption with Focused Ultrasound: Histological Findings in Rabbits*" Ultrasound in Med. Biol. vol. 31, No. 11, pp. 15271537, 2005.
P. Dayton et al. "*The Magnitude of Radiation Force on Ultrasound Contrast Agents*" J. Acoust. Soc. Am. 112, 2183-2192, 2000.
Tartis et al. "*Therapeutic Effects of Paclitaxel-Containing Ultrasound Contrast Agents*" Ultrasound in Med Biol Col. 32, No. 11, pp. 1771-1780, 2006.
Shortencarrier et al. "*A Method for Radiation-Force Localized Drug Delivery Using Gas-Filled Liposheres*" IEEE Transactions on Ultrasonics, Ferroelectrics, and Frequency Control, vol. 51, No. 7, Jul. 2004.
S. Maiti et al. "*Measuring Serotonin Distribution in Live Cells with Three-Photon Excitation*" Science, 275, 530-2 (1997).
B.J. Backsai et al. "*Chronic Imaging of Anzyloid Plaques in the Live Mouse Brain Using Multiphoton Microscopy*" Proc. Of SPIE, 4262, pp. 125-133 (2001).
Lewis et al. "*Therapeutic ultrasound Enhancement of Drug Delivery to Soft Tissues*" Int. Symp. Thera. Ultras, AIP Conf Proc. 2113, 403-407, 2009.
Lewis ct al. "*Development of a Portable Therapeutic and High Intensity Ultrasound System for Military Medical, and Research Use*" Review of Scientific Instruments, 79, 114302 (2008).
Lewis et al. "*Design and Characterization of a High-Power Ultrasound Driver with Ultralow-Output Impedance*" Review of Scientific Instruments 80, 114704, 2009.

(56) References Cited

OTHER PUBLICATIONS

Neeves et al. "*Fabrication and Characterization of Micolluidic Probes for Convection Enhanced Drug Delivery*" Journal of Controlled Release 111, pp. 252, 262 (2006).

S. Maruvada et al. "*Acoustic Power Calibration of High-Intensity Focused Ultrasound Transducers Using a Radiation Force Technique*"J. Acoustics Soc. Am. 121, pp. 1434-1439 (2007).

Lewis et al. "*Cost-Effective Broad-Bend Electrical Impedance Spectroscopy Measurement Circuit and Signal Analysis for Piezo-Materials and Ultrasound Transducers*" Measurement Science and Technology, 19, 1-7 (2008).

IEEE, "*Guide for Medical Ultrasound Field Parameter Measurements*" New York., IEEE 1990.

Alum, "*Acoustic Output Labeling Standard for Diagnostic Ultrasound Equipment: a standard for Now Manufacturers Should Specify Acoustic Output Data*" Am. Inst. Ultras. Med. 1998.

Blomley et al. "*WFUMB Safety Symposium on Ultrasound Contrast Agents: Clinical Applications and Safety Concerns*" Ultrasound Med and Biol. vol. 33, No. 2, pp. 180-186, 2007.

D. Dalecki "*WFUMB Safety Symposium on Echo-Confrast Agents" Bioelfects of Ultrasound Contrast Agents in VIVO* Ultrasound in Med and Biol. vol. 33, No. 2, pp. 205-213, 2007.

R. Carriles et al. "*Invited Review Article: Imaging Techniques for Harmonic and Multiphoton Adsorption Fluorescence Microscopy*" Rev. Sci, Inst. 80, 1-23, 2009.

W. Broaddus, et al. "*Distribution and Stability of Antisense Phosphorothioate Oligonucleotides in Rodent Brain Following Direct Intraparenchymal Controlled-Rate Infusion*" J. Neurosurge, 88: pp. 734-742 (1998).

G. Huynh et al. "*Barriers to Carrier Mediated Drug and Gene Delivery to Brain Tumors*" Journal of Controlled Release, 110, pp. 236-259 (2006).

W. Pitt "*Defining the Role of Ultrasound in Drug Delivery,*" Healthcare Technology Review, Am J Drug Delivery 1, pp. 27-42 (2003).

Shiran et al. "*Some of the Factors Involved in the Sarazyan Method for Recording Ultrasound Field Distributions with Special Reference to the Application of Ultrasound Physiotherapy*" Ultrasonics, 28, pp. 411-414 (1990).

S. Tiwari et al. "*A Review of Nanocarrier-Based CNS Delivery System*" Current Druge Delivery. 3, pp. 219-232 (2006).

* cited by examiner

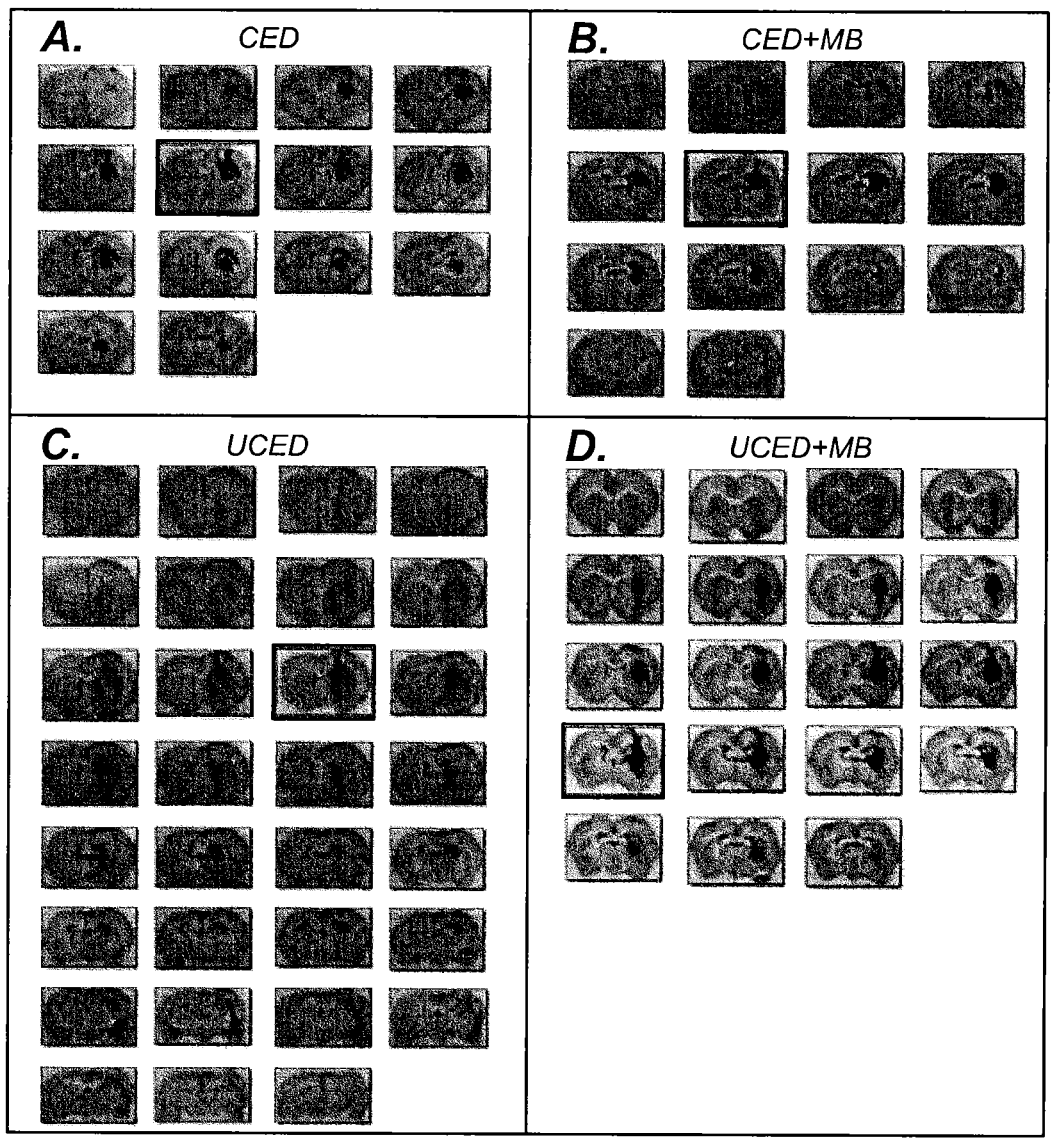
FIGS. 4A-D

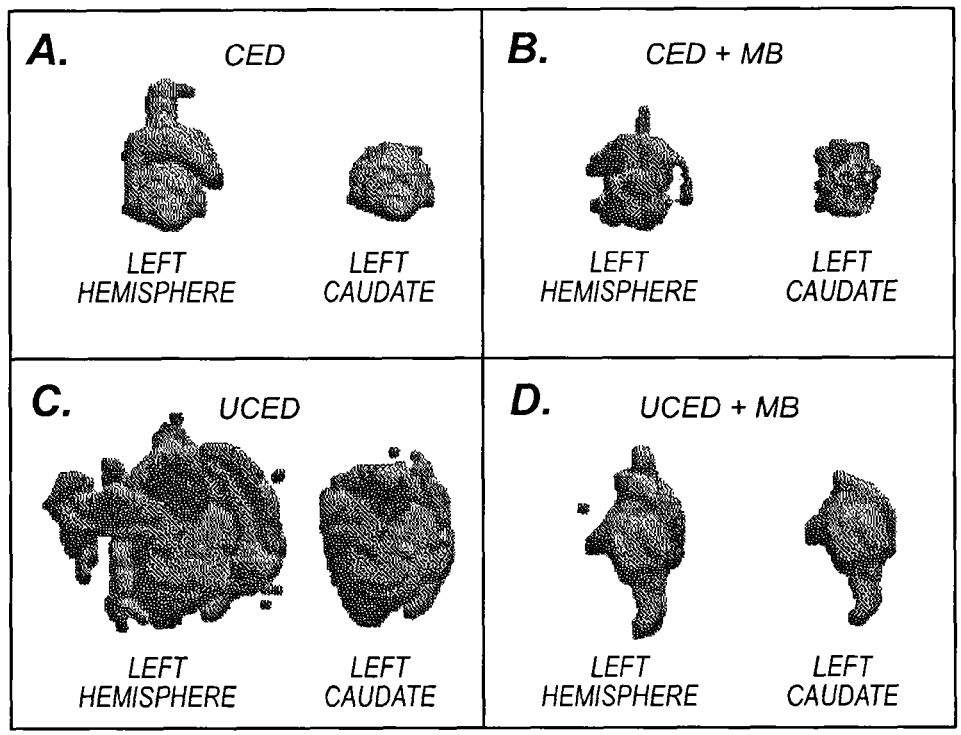
*FIG. 5A-D*
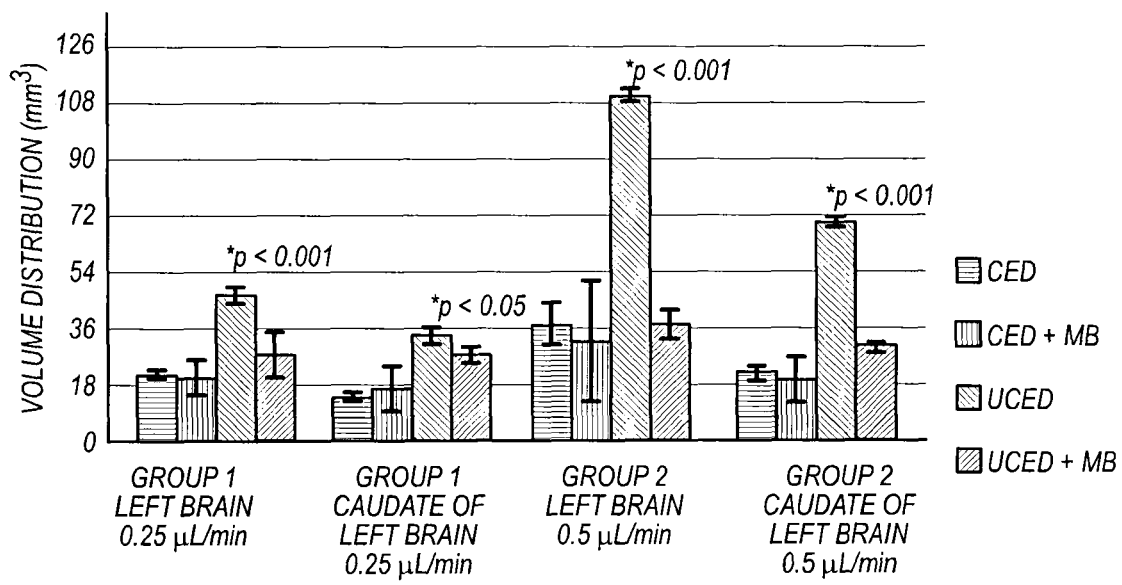
*FIG. 6*

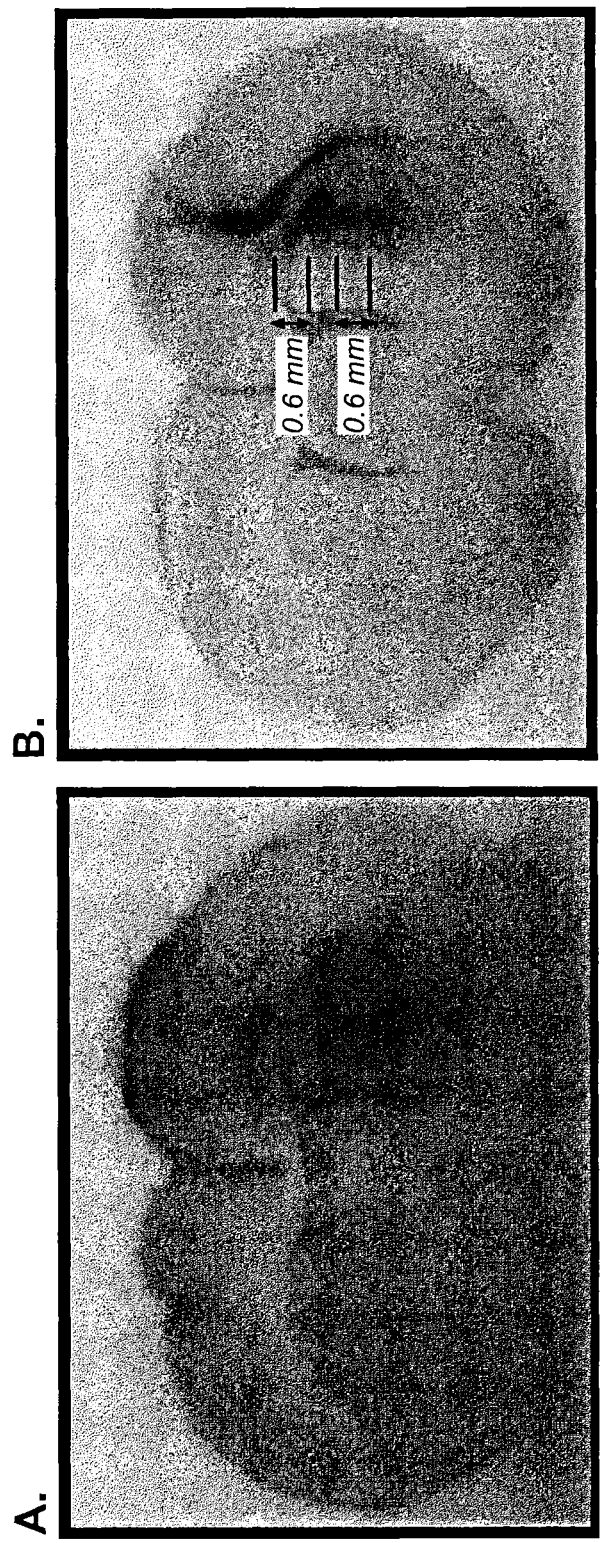
FIG. 12A-B

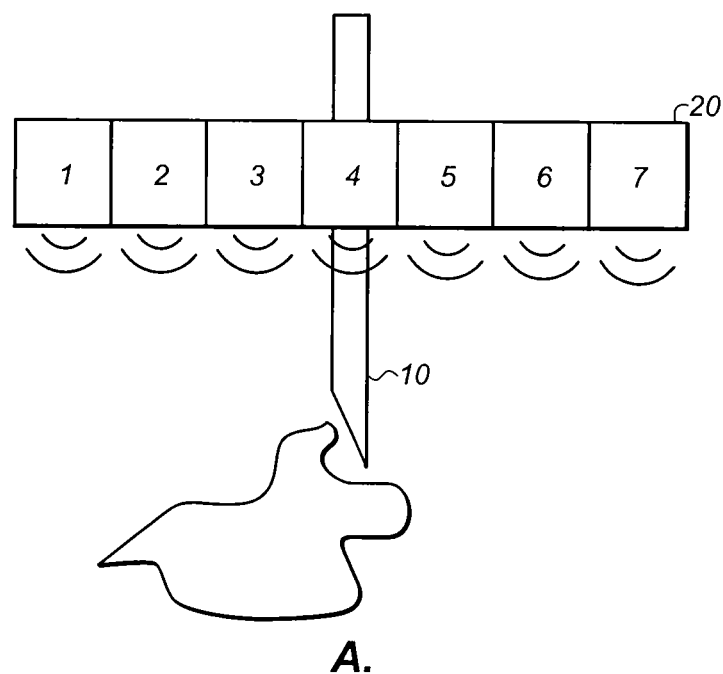
A.
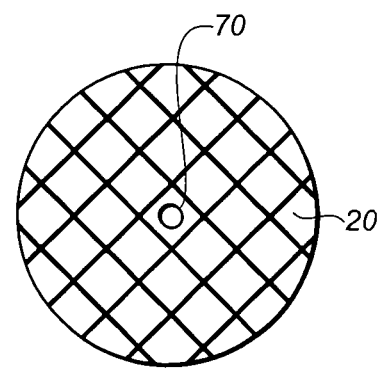
B.
FIG. 13A-B

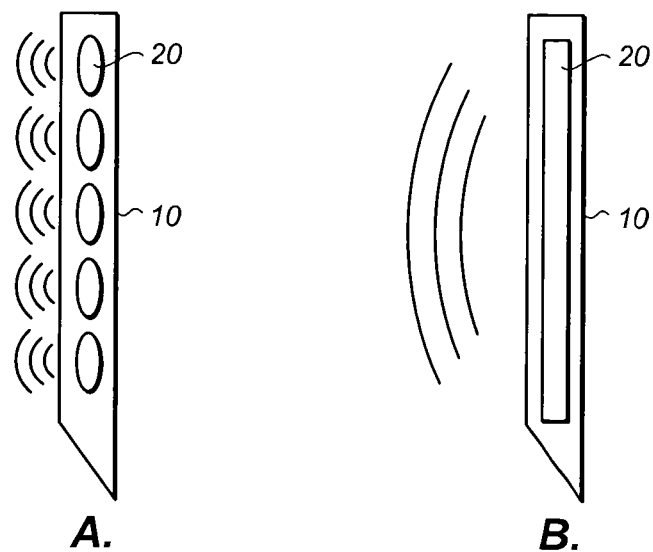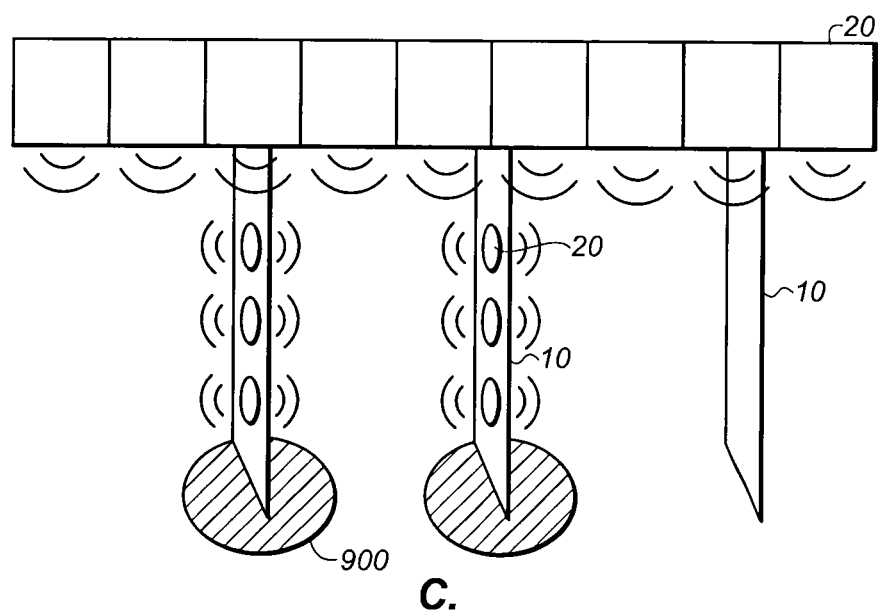
FIG. 14A-C

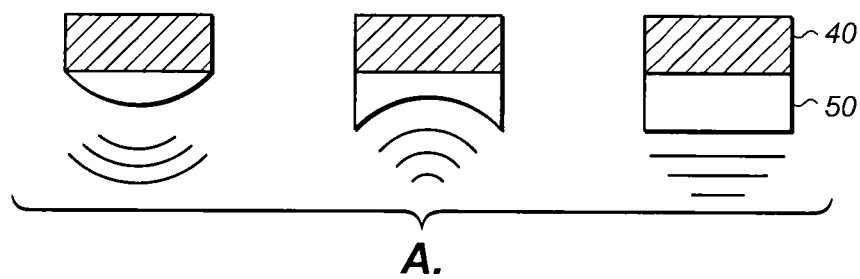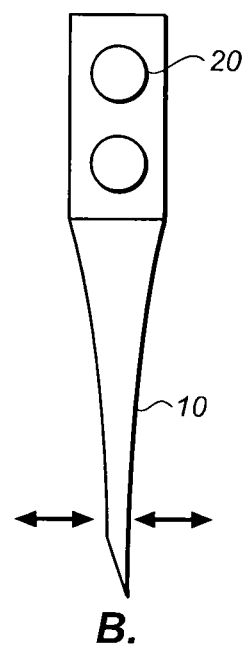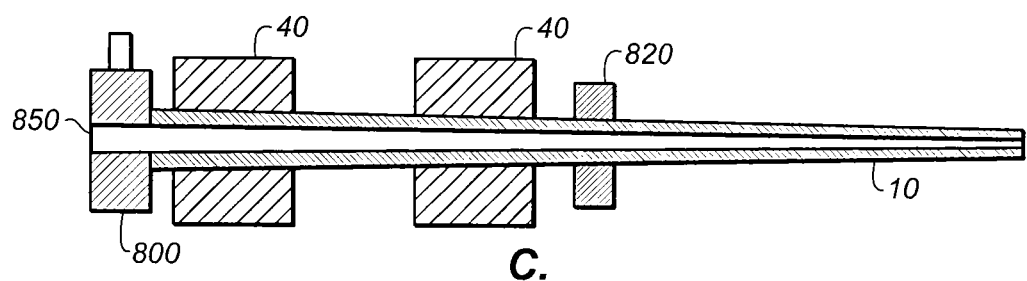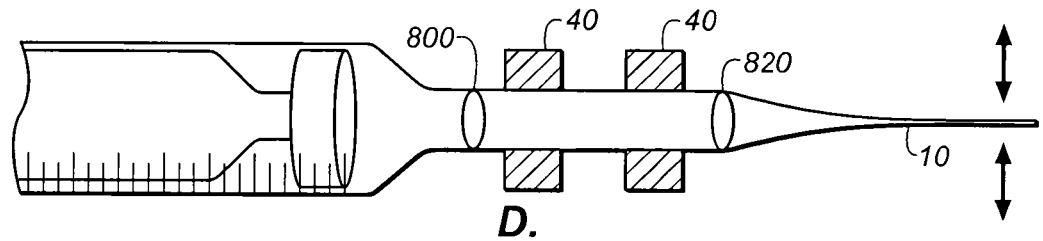
FIG. 15A-D

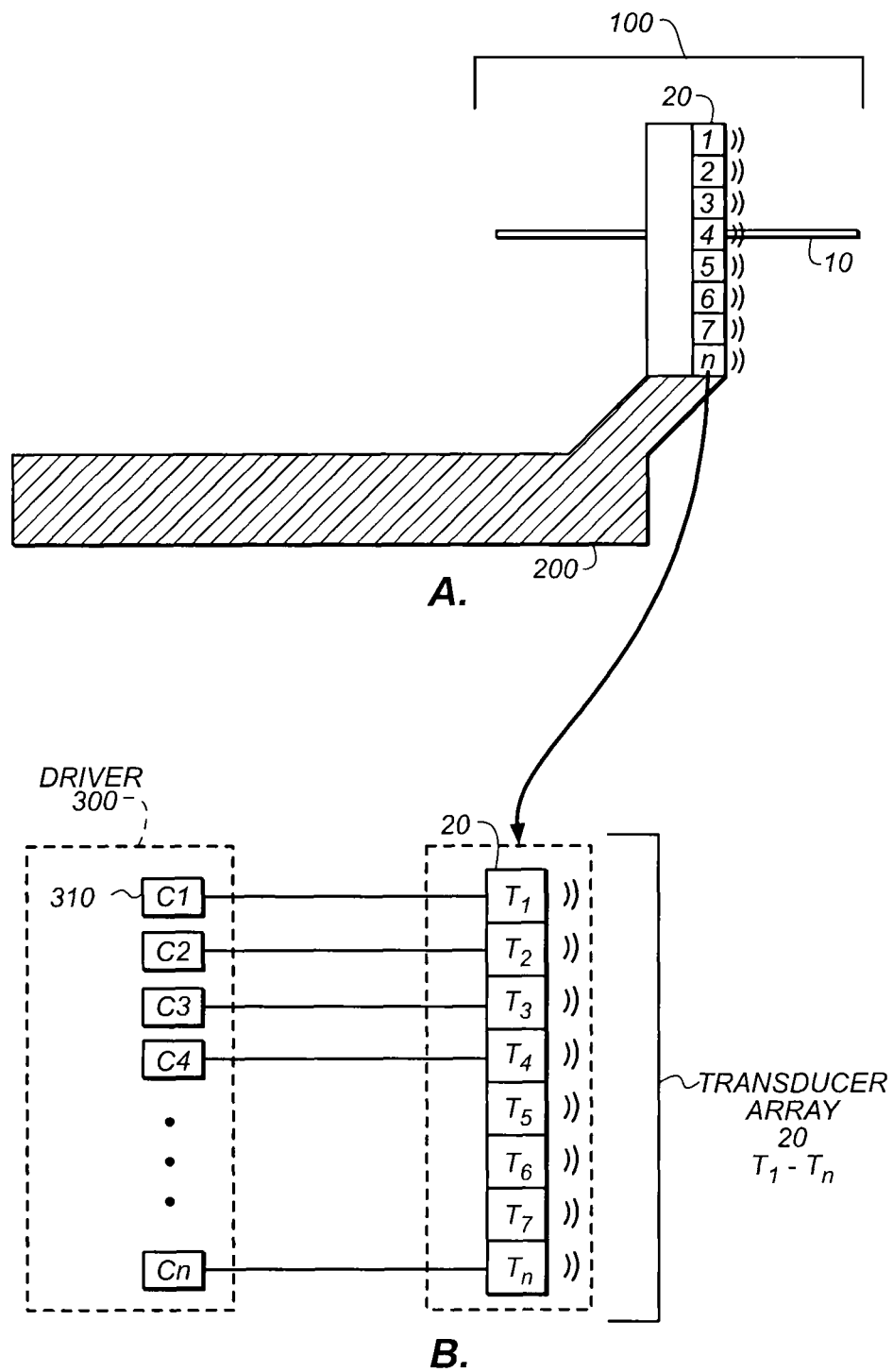
FIGS. 16A-B

ULTRASOUND-ASSISTED CONVECTION ENHANCED DELIVERY OF COMPOUNDS IN VIVO WITH A TRANSDUCER CANNULA ASSEMBLY

CROSS REFERENCE TO RELATED APPLICATIONS

This application is a National Stage application under 35 U.S.C. § 371 of PCT Application No. PCT/US2011/027238, filed Mar. 4, 2011, entitled "ULTRASOUND-ASSISTED CONVECTION ENHANCED DELIVERY OF COMPOUNDS IN VIVO WITH A TRANSDUCER CANNULA ASSEMBLY" which claims priority to and the benefit of U.S. provisional patent application Ser. No. 61/311,064, entitled Ultrasound Assisted Brain Drug Delivery Cannula, filed Mar. 5, 2010, which is incorporated herein by reference in its entirety.

STATEMENT REGARDING FEDERALLY SPONSORED RESEARCH OR DEVELOPMENT

Not applicable

1. TECHNICAL FIELD

The present invention relates to methods and apparatuses for delivering a compound to a targeted cell, tissue, organ or region of the body in a subject. The present invention also relates to methods and apparatuses for treating a disease or disorder by delivering a compound directed against the disease or disorder to a targeted cell, tissue, organ or region of the body in a subject.

2. BACKGROUND OF THE INVENTION

In convection-enhanced delivery (CED), drugs are infused locally into tissue through a cannula inserted into the tissue. Transport of the infused material is dominated by convection, which enhances drug penetration into tissue compared with diffusion mediated delivery. One drawback of CED is that larger proteins and compounds may interact with components of the extracellular matrix and/or cell membrane, resulting in inhibition of their transport. These compounds may also be cleared by capillaries, internalized by untargeted cells, or enzymatically degraded, thus not reaching their target.

Brain tissue is more poroelastic in that it deforms in response to local pressure. Pressure associated with infusion by needles can cause the brain tissue to separate away from the needle, opening a gap for material to flow back out. Conventional CED eliminates most of this deformation, but the area of delivery is still limited as noted above.

CED has emerged as a leading investigational delivery technique for the treatment of several disorders, including glioblastoma multiforme, a high-grade glioma that presents an especially poor prognosis for patients. CED bypasses the blood-brain barrier by infusing compounds through a needle or microcatheter directly into brain parenchyma or brain tumor. The clinical trials show mixed results and suggest that the outcome of the therapy depends strongly on the extent of penetration of the drug into the brain, which is determined by infusion velocity, the relative rates of convection and elimination during CED, and tissue properties. To increase the infusion velocity special micro-catheter and flexible designs have been constructed to reduce backflow of drug between the tissue and needle-shaft interfaces. To reduce the elimination rate and thereby extend the penetration distance, infused compounds have been incorporated into nanoparticles such as liposomes or polymeric beads, which protect the compounds during transport. However, backflow of drug during CED treatment still remains a critical problem in clinical practice and the transport of nanoparticles through the brain is hindered, because the size of the nanoparticles is comparable to the size of a typical "pore" of the extracellular space. Furthermore, it can be difficult to control the spatial distribution of infused molecules and nanoparticles when tissue characteristics vary within the treatment region, such as in heterogeneous tissue and near white matter tracts in the brain. There is therefore a need in the art for a delivery device that reduces backflow, increases the penetration distance and provides control over the spatial distribution of the infused drug. Such a delivery device could significantly improve the efficacy of CED in clinical practice.

Citation or identification of any reference in Section 2, or in any other section of this application, shall not be considered an admission that such reference is available as prior art to the present invention.

3. SUMMARY OF THE INVENTION

An ultrasound transducer cannula assembly (TCA) apparatus is provided comprising a cannula and an ultrasound transducer, wherein activation of the ultrasound transducer creates an acoustic field around, within and/or through the cannula.

In one embodiment, the cannula comprises the ultrasound transducer.

In another embodiment, the apparatus comprises a second cannula for guiding the cannula ("guide cannula").

In another embodiment, the ultrasound transducer comprises portions defining a hole, canal or groove for positioning of the cannula.

In another embodiment, the ultrasound transducer can have portions defining a plurality of holes, canals or grooves for positioning of a plurality of cannulas.

In another embodiment, the apparatus can comprise a wired or wireless interface.

In another embodiment, the ultrasound transducer comprises a piezoelectric material.

In another embodiment, the piezoelectric material is a piezoelectric ceramic, piezoelectric crystal, lead zirconate titanate (PZT) or polyvinylidene fluoride (PVDF).

In another embodiment, the ceramic is a lead zirconate-titanate (PZT-4).

In another embodiment, the apparatus comprises a stereotaxic, manual or robotically controlled guide arm.

In another embodiment, the ultrasound transducer comprises electrodes, and the electrodes are operably connected to the ultrasound transducer and to the ultrasound driver.

In another embodiment, the cannula is an infusion needle, catheter, microcatheter or microfabricated catheter.

In another embodiment, the cannula is disposable.

In another embodiment, the inner diameter of the cannula is 500 nm-3 mm.

In another embodiment, the ultrasound transducer ultrasonically activates the cannula.

In another embodiment, the cannula produces ultrasound.

In another embodiment, the ultrasonic activation of the cannula vibrates or moves the cannula.

In another embodiment, the apparatus is an implantable apparatus.

In another embodiment, the apparatus comprises a plurality of cannulas or a plurality of ultrasound transducers.

In another embodiment, the plurality of ultrasound transducers are arranged in an array.

In another embodiment, a member of the plurality of ultrasound transducers produces a different frequency of ultrasound from another member of the plurality of ultrasound transducers.

In another embodiment, the frequency produced by one member of the plurality of ultrasound transducers and the frequency produced by another member of the plurality of ultrasound transducers have different bioacoustical qualities.

In another embodiment, the apparatus produces a standing wave or acoustic field.

In another embodiment, the plurality of ultrasound transducers is positioned in an array on the cannula.

In another embodiment, the plurality of ultrasound transducers is positioned in an array on one or more cannulas in the plurality.

In another embodiment, the apparatus comprises a housing for the ultrasound transducer.

In another embodiment, the housing is a biocompatible material.

In another embodiment, the biocompatible material is aluminum, titanium, stainless steel, acrylic, polystyrene or polyetherimide (PEI) thermoplastic.

In another embodiment, the apparatus comprises an ultralow output impedance ultrasound driver wherein the driver produces an ultrasound drive signal waveform; and a connection between the ultrasound driver and the ultrasound transducer.

In another embodiment, the ultralow output impedance ultrasound driver is microprocessor-controlled.

In another embodiment, the ultralow output impedance ultrasound driver comprises a printed circuit board (PCB) comprising a plurality of surface-mounted metal-oxide-semiconductor field-effect transistors (MOSFETs), wherein the MOSFETs are positioned in parallel or independent configuration and wherein the MOSFETs drive a single piezoelectric transducer channel or multiple independent piezoelectric transducer channels In another embodiment, the MOSFETs are configured in a transistor-transistor logic (TTL) timing configuration to drive single or multiple independent channels.

In another embodiment, the driver comprises an onboard microprocessor controller for monitoring and/or controlling ultrasound parameters.

In another embodiment, the apparatus can comprise a user interface and software for monitoring acoustic energy produced by the ultrasound transducer, adjusting power produced by the ultrasound transducer, and/or modulating the ultrasound drive signal waveform.

In another embodiment, the microprocessor controller controls a single or multiple independent channels.

In another embodiment, the microprocessor controller measures ultrasound output energy.

In another embodiment, the driver comprises a waveform generator integrated circuit (IC); and the waveform generator IC is interfaced with the microprocessor controller, thereby creating a timing transducer or function generator.

In another embodiment, the driver additionally comprises a user interface and software for monitoring acoustic energy (ultrasound output energy), adjusting power, and/or modulating the ultrasound drive signal waveform.

In another embodiment, the driver has pulse width and drive signal frequency modulation of a TTL timing signal produced by the driver.

In another embodiment, the driver has real-time onboard electrical power output measurement from the driver.

In another embodiment, the driver has computer and/or onboard control of the MOSFET switching power supply.

In another embodiment, the driver comprises a driver overload monitor

In another embodiment, the driver is battery powered.

A method for ultrasound-assisted convection-enhanced delivery (UCED) of a compound to a targeted cell, tissue, organ or region of the body (hereinafter "target") in a subject is also provided. The method can comprise the steps of providing an ultrasound transducer cannula assembly (TCA) apparatus; contacting the ultrasound TCA apparatus to the target; introducing the compound (or a solution thereof) into cannula; activating the ultrasound transducer, thereby producing an acoustic field; and releasing the compound from the cannula, whereby the compound contacts the target.

In another embodiment, the target is in a diseased state or subject to a medical disorder.

In another embodiment, the steps of activating the ultrasound transducer and releasing the compound are concurrent.

In another embodiment, the step of activating the ultrasound transducer is after the step of releasing the compound.

In another embodiment, the step of activating the ultrasound transducer is before the step of releasing the compound.

In another embodiment, the step of activating the ultrasound transducer and producing an acoustic field produces an acoustic field around, within, through or outside of the cannula.

In another embodiment, the contacting step comprises stereotactically, manually or robotically guiding the ultrasound TCA apparatus to the target.

In another embodiment, the activating step comprises adding stabilized microbubbles to the compound.

In another embodiment, the compound is encapsulated and the step of activating the ultrasound transducer and producing an acoustic field breaks the encapsulation and releases the encapsulated compound.

In another embodiment, the compound is encapsulated by a lysosome, liposome, micelle, microbubble, stabilized microbubble or wherein the compound is a coated (e.g., polymer coated) nanoparticle.

In another embodiment, a plurality of compounds are delivered to the target. In one embodiment, each compound in the plurality can be delivered by a different cannula. In another embodiment, a single cannula can deliver a plurality of compounds.

In another embodiment, at least one member of the plurality of compounds is encapsulated and the step of activating the ultrasound transducer and producing an acoustic field breaks releases the encapsulated compound and/or mixes it with another member of the plurality of compounds.

In another embodiment, the step of activating the ultrasound transducer diminishes or skews the subject's perception of pain.

In another embodiment, the step of activating the ultrasound transducer to diminish or skew the subject's perception of pain is before the step of contacting the ultrasound TCA apparatus to the target.

In another embodiment, the step of activating the ultrasound transducer produces a standing waveform or focused field.

A method for making an ultrasound transducer cannula assembly (TCA) apparatus comprising the steps of:

providing a cannula, a piezoelectric material with two electrically conducting surfaces, an electrical conductor, and a housing with a transducer face;

fashioning an ultrasound transducer from the piezoelectric material, wherein the ultrasound transducer comprises portions defining a hole, canal or groove for positioning of the cannula;

attaching the electrical conductor to the ultrasound transducer face, wherein the electrical conductor is electrically isolated from one of the two conducting surfaces of the piezoelectric material;

positioning the ultrasound transducer within the housing;

positioning the cannula through the positioning hole, canal or groove; and attaching the cannula to the ultrasound transducer.

In one embodiment, the method comprises the step of providing a guide cannula, wherein the step of positioning the cannula comprises inserting the cannula through the guide cannula.

In another embodiment, the method further comprises the step providing a guide arm and assembling the housing with guide arm, wherein the housing houses the ultrasound transducer.

In another embodiment, the method comprises the step of providing connecting cables or wires and attaching the cables or wires to the ultrasound transducer positioned in the housing assembled with the guide arm.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1A. Schematic of a method for constructing one embodiment of the transducer cannula assembly (TCA) 100 of the ultrasound TCA apparatus 1000. I. The ultrasound transducer 20 is fashioned from a disk of piezoelectric material 40 with a cutout center hole 70. In this embodiment, PZT-4 ceramic is machined into a disk with a center hole. II. An electrical conductor 30, in this embodiment a brass tube, is connected to the front face of the disk of piezoelectric material 40 using solder. In this embodiment, the electrical conductor 30 (in this embodiment, also functioning as the needle guide) is electrically isolated from (does not touch) one of the two metal surfaces coating the piezoelectric material. The electrical conductor 30 makes an electrical connection with the second metal surface. III. The electrical conductor 30 is attached to the face of the housing (in this embodiment, an aluminum standoff) of the ultrasound transducer 20. IV. The ultrasound transducer 20 is placed in a watertight housing 50 (in this embodiment, aluminum or PVC plastic) and in association with the guide arm 200. V. The piezoelectric disk 40 of the ultrasound transducer 20 is connected with coaxial cable that runs through the guide arm 200 (in this embodiment, a stereotaxic guide arm). Ground and hot leads 80 are connected to the ultrasound transducer 20 through the guide arm 200. VI. The cannula 10 (also referred to herein as an "infusion cannula") and the guide cannula 60 are inserted (in this embodiment, inserted through the electrical conductor 30) and attached to the ultrasound transducer 20 and secured to the proper height with epoxy or dental cement or other suitable glue or fastener. VII. The completed ultrasound transducer cannula assembly (TCA) 1000. See Section 6.1 for details.

Figure 1B:
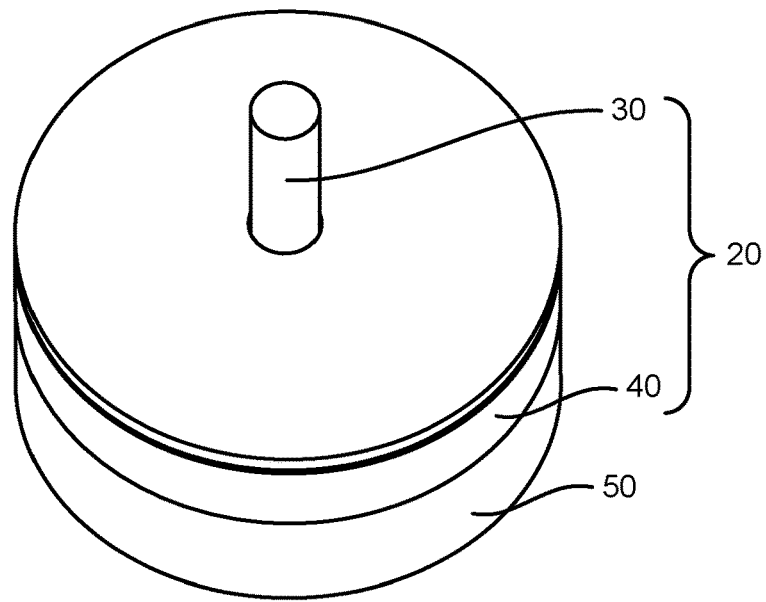

FIG. 1B. Close up photograph of the ultrasound transducer 20, showing the piezoelectric material 40 (in this embodiment, a piezoelectric ceramic disk) and the electrical conductor 30 (also the needle guide in this embodiment), mounted on a standoff on the housing 50 (in this embodiment, an aluminum standoff and housing.)

Figure 1C:
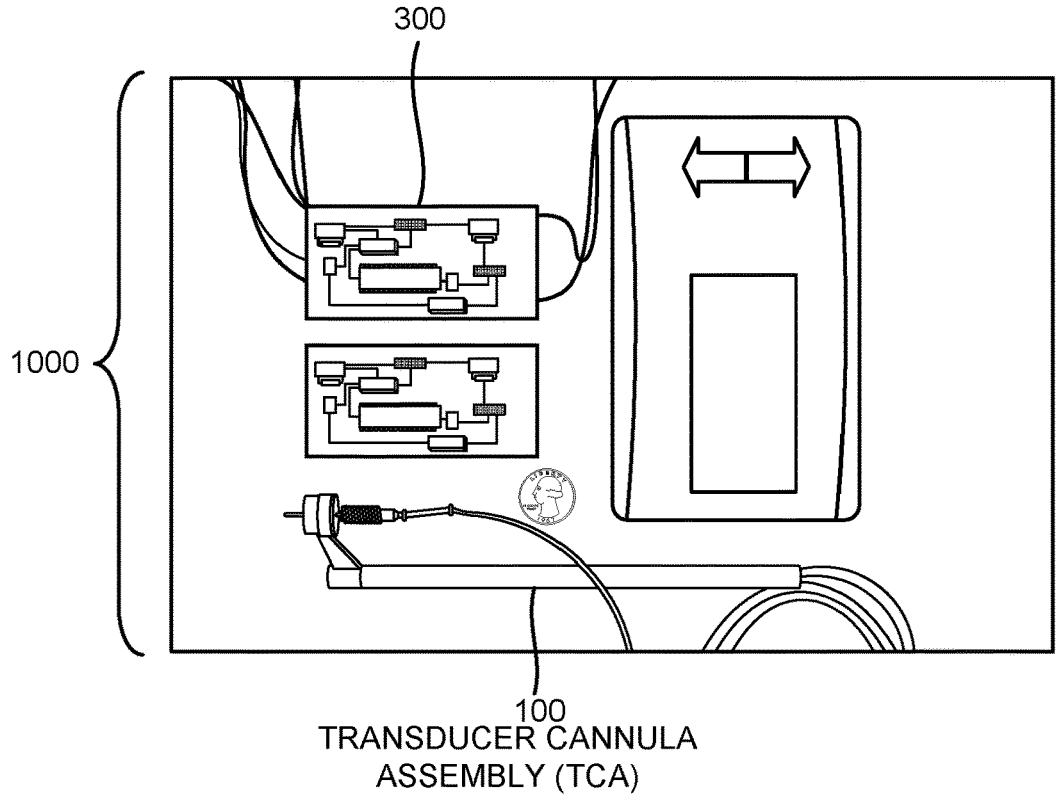

FIG. 1C. Photograph of one embodiment of the ultrasound TCA apparatus 1000 showing the ultralow out impedance ultrasound driver and printed circuit board (PCB) 300 and the transducer cannula assembly (TCA) 100.

Figure 2:
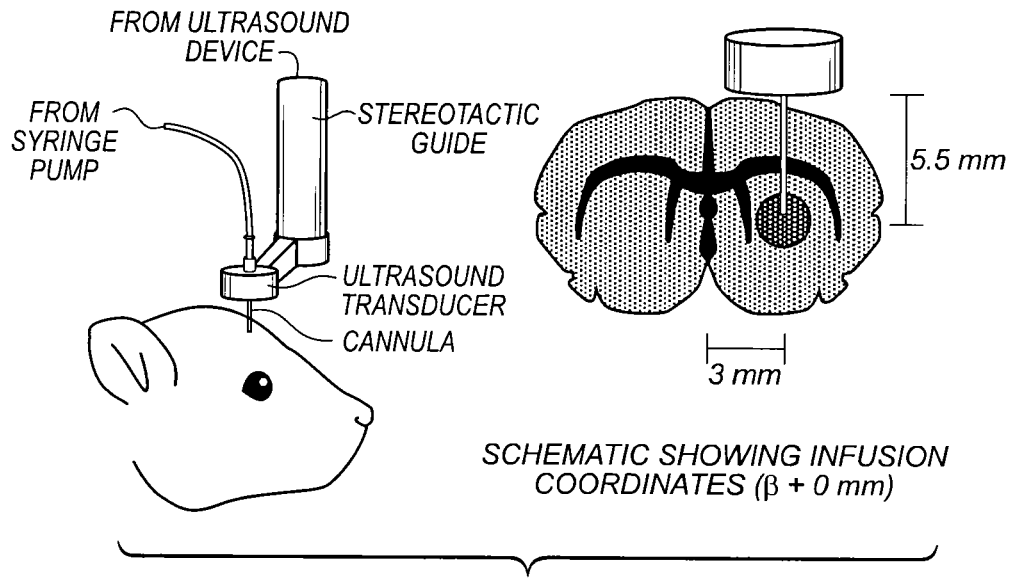

FIG. 2. Animal experimental setup for testing the ultrasound TCA apparatus in the rat brain. The rat was secured with ear bars in a stereotaxic frame and a small craniotomy was performed on the left hemisphere. The TCA was guided 5.5 mm deep into the caudate of the rat brain. See Section 6.1 for details.

Figure 3:
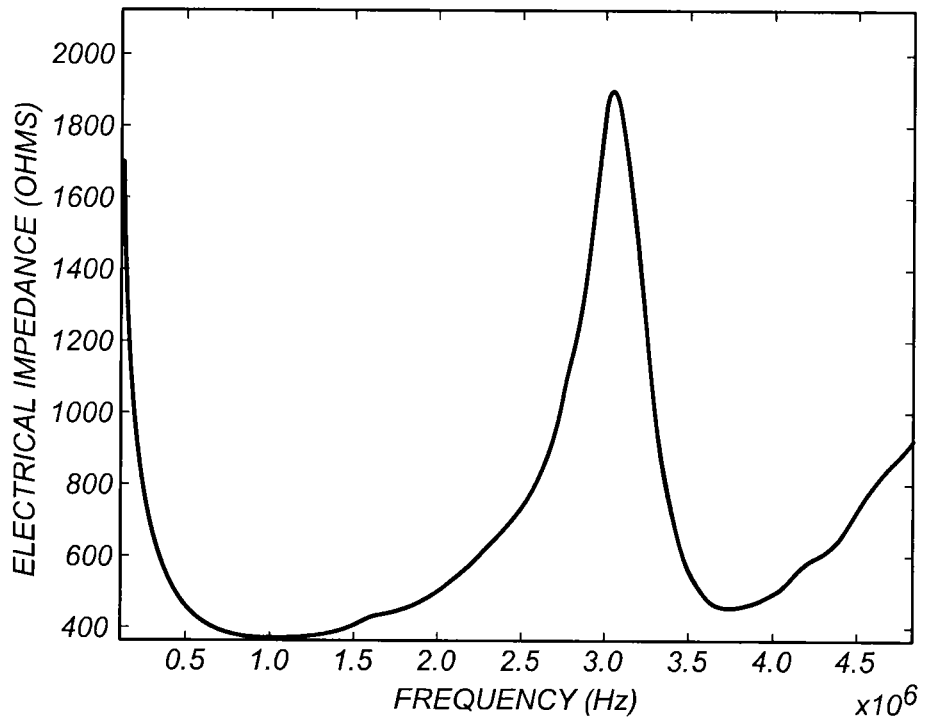

FIG. 3. Determination of electrical impedance in one embodiment of the TCA. Resonance occurs at 1.18 MHz with 380Ω impedance. The phase angle (not shown) is approximately 0 degrees at resonance. Parallel resonance occurs at 3.1 MHz. See Section 6.1 for details.

FIGS. 4A-D. Brain sections from the four subgroups of Group 2 rats studied after 30 minutes of Evans blue dye (EBD) infusions at 0.5 µl per minute with a 30 gauge cannula. A. Convection enhanced delivery (CED). B. CED with microbubbles (CED+MB). C. Ultrasound-assisted convection enhanced delivery (UCED). D. Ultrasound-assisted convection enhanced delivery with microbubbles (UCED+MB). See Section 6.1 for details.

FIGS. 5A-D. Three-dimensional infusion reconstruction of the four subgroups of Group 2 brain sections from FIGS. 4A-D. The cannula is in the plane of the figure and the transducer cannula assembly (TCA) is positioned at the top of each figure. A. Convection enhanced delivery (CED). B. CED with microbubbles (CED+MB). C. Ultrasound-assisted CED (UCED). D. Ultrasound-assisted CED with microbubbles (UCED+MB). See Section 6.1 for details.

FIG. 6. Analysis of total Evans blue dye (EBD) volume distribution in the rodent brain with subgroup standard error bars. UCED and UCED+MB increases EBD volume distribution by 2.24× and 1.37× in the left hemisphere and 2.44× and 1.70× in the left caudate, respectively, as compared with CED and CED+MB receiving 0.25 µL per min infusions. For 0.5 µL per min infusions of group 2, UCED and UCED+MB increases EBD volume distribution by 2.96× and 1.16× in the left hemisphere and 3.25× and 1.54× in the left caudate, respectively. The left hemisphere and left caudate subgroups of groups 1 and 2 are statistically significant with independent means $p<0.05*$ and $p<0.001*$. For each group in the bar graph, first bar is CED, second bar is CED+MB, third bar is UCED and fourth bar is UCED+MB. See Section 6.1 for details.

Figure 7:
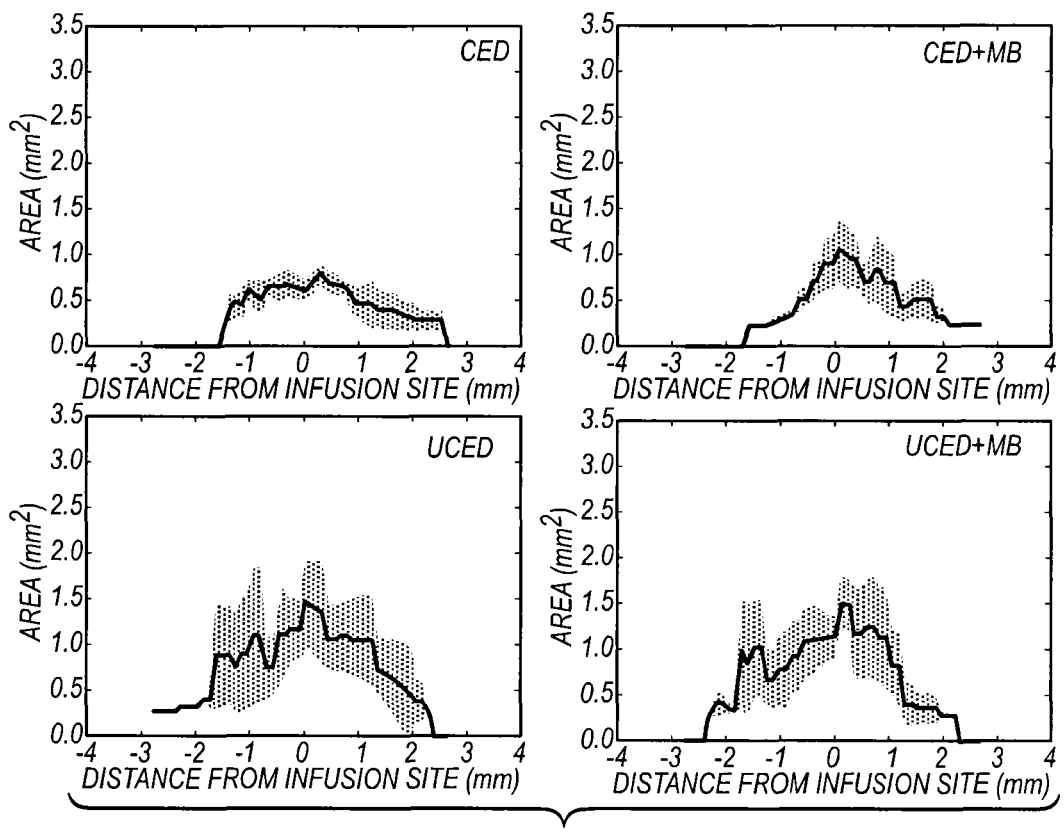

FIG. 7. Group 1. 0.25 µL per min infusion analysis of EBD distribution profile in the rodent caudate as a function of the anterior-posterior (AP) distance in the region ±4 mm from the infusion site. The black line represents the average area of EBD at the given position. The shaded region represents the standard deviation of EBD area (n=5). See Section 6.1 for details.

Figure 8:
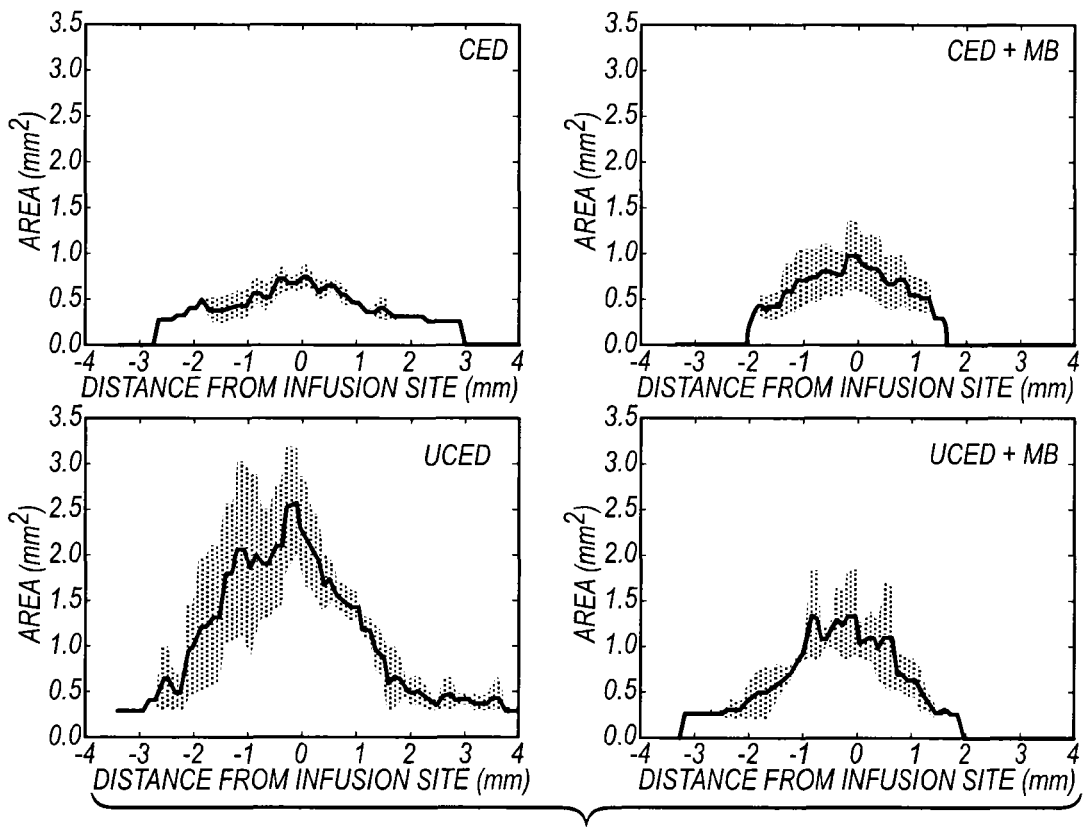

FIG. 8. Group 2. 0.5 µL per min infusion. Analysis of EBD distribution profile in the rodent caudate as a function of the AP distance in the region ±4 mm from the infusion site. The black line represents the average area of EBD at the given position. The shaded region represents the standard deviation of EBD area (n=5). See Section 6.1 for details.

Figure 9:
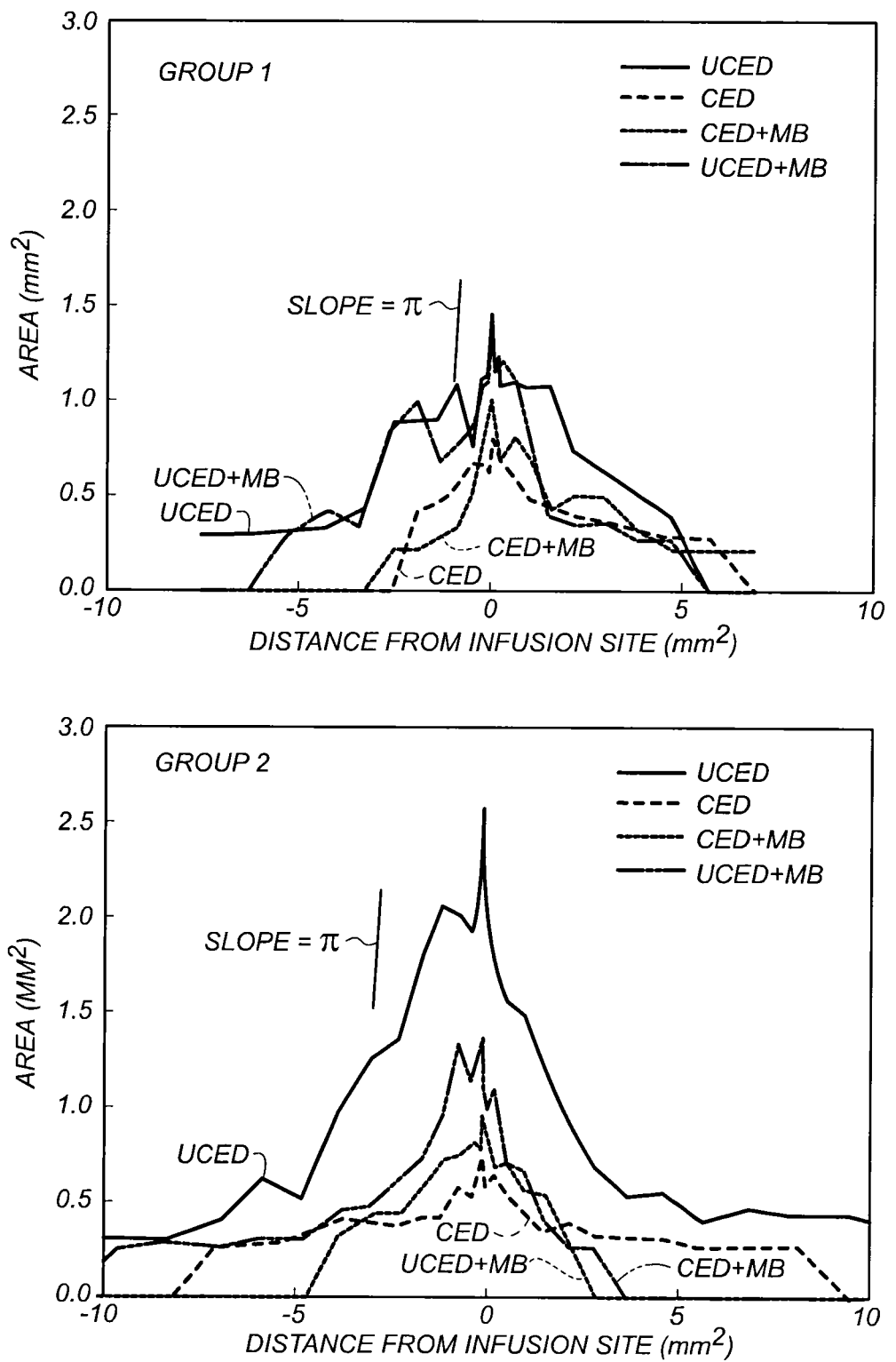

FIG. 9. The area of EBD in rodent caudate for each slice plotted as a function of the square of the AP for Group 1 and Group 2. Each solid line is the average area for each treatment at the given position. A dotted line segment with a slope magnitude of π is drawn for reference. Data that fall on a line with slope of π or –π indicate regions where the infusion of EBD is locally isotropic. Deviations from the slope indicate an anisotropic volume distribution. See Section 6.1 for details.

Figure 10:
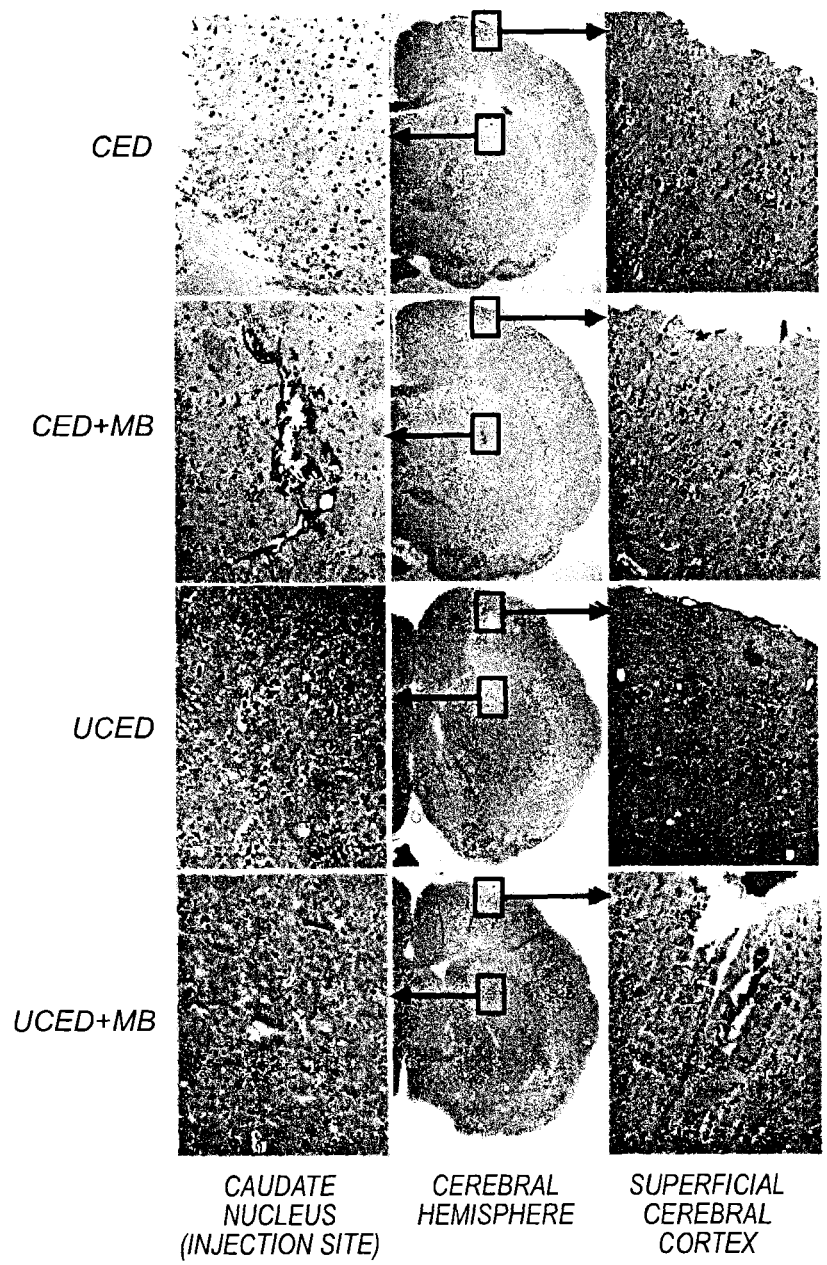

FIG. 10. Hematoxylin and eosin stain of rodent brains (10 μm coronal slices) in the cannula insertion path. CED, CED+MB, UCED and UCED+MB show similar histological results in both the cortex and caudate of the rodent brains. Mild parenchymal disruption, edema and hemorrhage around the needle track and injection site are equivalent for the group. See Section 6.1 for details.

Figure 11:
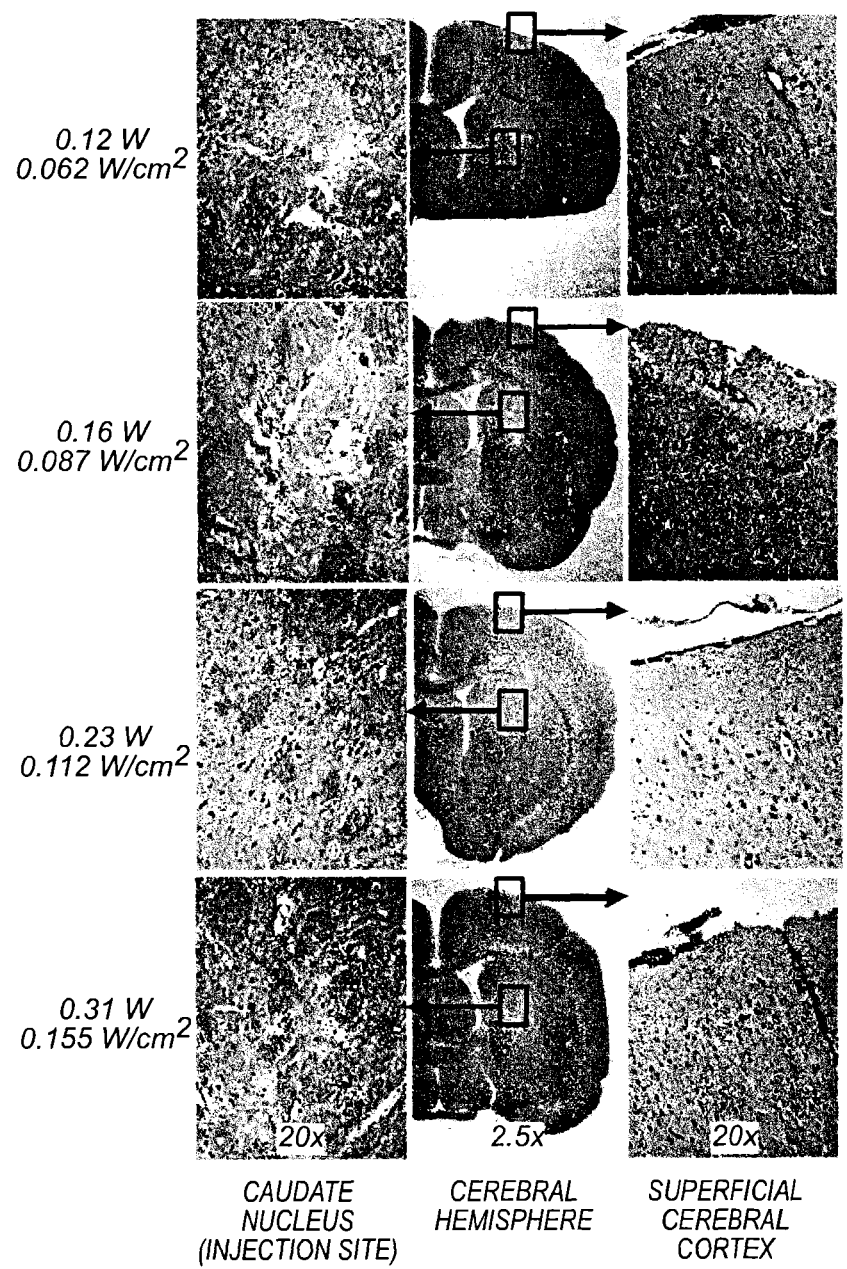

FIG. 11. Hematoxylin and eosin stain of rodent brains (10 μm coronal slices) in the cannula insertion path. Acoustic intensities of 0.062, 0.087, 0.112 and 0.155 W/cm$^2$ show similar histological results in both the cortex and caudate of the rodent brains. Mild parenchymal disruption, edema and hemorrhage around the needle track and injection site are equivalent for the group. See Section 6.2 for details.

FIGS. 12A-B. UCED infusion profiles. The rat brain in (A) shows a relatively uniform distribution, while the brain in (B) shows clear banding of the infused dye approximately 0.6 mm apart. See Section 6.2 for details.

FIGS. 13A-B. Schematics of: A. An ultrasound TCA comprising a plurality of ultrasound transducers 20 in a two-dimensional array. Cannula 10. B. Top view of the array of ultrasound transducers 20. Hole for cannula 70.

FIGS. 14A-C. Schematics of: A. A plurality of ultrasound transducers 20 in an array on a cannula 10. B. A long, thin rectangular (strip) shaped ultrasound transducer 20 that can be mounted inside or outside of a cannula 10. C. An ultrasound TCA comprising a plurality of ultrasound transducers 20 in a two-dimensional array. Additional ultrasound transducers 20 are positioned in arrays on two of the cannulas 10 (left and middle), from each of which a compound 900 is being infused.

FIGS. 15A-D. Schematics of: A. Concave, convex and flat housings 50 covering the piezoelectric material 40 in three embodiments of an ultrasound TCA. The different shapes of the housings can act as lenses to control or focus the ultrasound waves and acoustic fields produced. B. Two ultrasound transducers 20 mounted on a cannula 10. The ultrasound produces a vibration in the cannula. C. An embodiment of a TCA comprising two piezoelectric elements 40 mounted between a syringe connector 800 and a needle connector 820 (e.g., Luer-Lock). Needle cannula 10. Fluid port 850. D. The embodiment of the TCA of (C) shown mounted on a syringe and vibrating the needle.

FIGS. 16A-B. Schematics of: A. Ultrasound TCA 100 with an array of n ultrasound transducers 20 in one row of an n×n two dimensional array. Guide arm 200. B. Each transducer 20 in the array is operably connected to a single channel 310 ("c1," "c2," etc.) in the ultralow output impedance ultrasound driver 300.

5. DETAILED DESCRIPTION OF THE INVENTION

A method for targeted delivery of a compound and an apparatus for use with the method are provided. This apparatus is referred to herein as an ultrasound transducer cannula assembly (TCA) apparatus or an ultrasound-assisted convection enhanced delivery (UCED) device. The ultrasound TCA apparatus is a cannula enhanced delivery (CED) device enhanced with an ultrasound system to enhance penetration of molecules in the target. The apparatus can be used for the delivery of a compound to a target in the body (e.g., a cell, tissue or organ of interest). In one embodiment, the ultrasound TCA apparatus comprises a transducer cannula assembly (TCA) and an ultrasound system. The ultrasound system may be portable and pocket-sized.

The use of ultrasound with CED in the ultrasound TCA apparatus improves the distribution volume of material, in some embodiments, four to six times over a CED device without ultrasound. The ultrasound TCA apparatus can be used for treatment of difficult-to-cure diseases, such as certain forms of cancer or tumors (e.g., glioblastoma multiforme of the brain) in which the majority of tumor is typically removed, but not the margins. The ultrasound TCA apparatus can be used for delivering and focusing compounds directed against those remaining cells to help prevent the recurrence of the disease. An additional benefit of using the ultrasound TCA apparatus for delivery of a compound of interest is that since the targeting can be more focused, less compound is needed, thus a lower potential for harmful effects to the host and host cells.

For clarity of disclosure, and not by way of limitation, the detailed description of the invention is divided into the subsections set forth below.

5.1 Ultrasound Transducer Cannula Assembly (TCA) Apparatus

An ultrasound transducer cannula assembly (TCA) apparatus is provided for delivering a compound of interest to a target. Any compound known in the art that can be prepared as a liquid infusate is suitable for delivery, including but not limited to drugs, pharmaceutical compositions, tracers, contrast agents, nanoparticles (e.g., 10-100 nm), liposomes and small interfering RNA (siRNA).

The target can be any cell, tissue or organ of interest in a eukaryotic (multicellular) subject. The target can be in a normal or healthy state or be in a state of disease or medical disorder (e.g., cancer or tumor). In one embodiment, the subject is a mammal, e.g., a human, a domestic animal, companion animal, etc.

The ultrasound TCA apparatus can comprise one or more cannulas (also referred to herein as "infusion cannula(s)") and one or more ultrasound transducers. The ultrasound TCA apparatus can also comprise an ultralow output impedance ultrasound driver, which is described in Section 5.2. The activation of the ultrasound transducer(s) by the driver creates an acoustic field around, within and/or through the cannula. The apparatus can therefore act as an axial or lateral (or combination of both types) resonating device that provides a cylindrical, focused or arbitrary-shaped (i.e., a desired shape) therapeutic acoustic field around the cannula during stereotaxic guided CED treatment.

FIG. 1A shows the assembly of one embodiment of the ultrasound TCA 100 of an ultrasound TCA apparatus 1000, comprising one cannula 10 and one ultrasound transducer 20, which is further described in Section 6.1, Example 1.

The cannula 10 can be any suitable cannula known in the art, such as an infusion needle, a catheter or a micro- (or microfabricated) catheter, all of which are commercially available. An art-known, suitable inner diameter of the infusion needle, catheter or microcatheter can be selected for the subject and target tissue, and typically, the inner diameter can range from 500 nm-3 mm. In one embodiment, a microfabricated catheter with, e.g., a 10-100 μm inner diameter, can be used. In another specific embodiment, a stainless steel cannula ranging from 10 to 32 gauge (ga) in size can be used.

In another embodiment, the ultrasound transducer 20 is cylindrical and the acoustic field it produces is axial or cylindrical. In other embodiments, the ultrasound transducer 20 and/or the housing or face of the transducer 50 can have another suitable shape, e.g., semi-cylindrical, square, rectangular, lenticular (e.g., on the face of the transducer to diverge energy over a broader area), etc. to produce acoustic fields of another desired shape (FIG. 15A). Suitable shapes can be determined and analyzed using methods disclosed hereinbelow and known in the art.

In another embodiment, the ultrasound transducer produces an acoustic field, around, surrounding, within or through the cannula. In certain embodiments, the cannula can be made to resonate by the ultrasound transducer so that the cannula produces ultrasound. In another embodiment, the cannula can serve as an ultrasound wave guide.

The ultrasonic activation of the cannula can vibrate or move the cannula (FIG. 15B). Such movement of the cannula can assist in the insertion of the ultrasound TCA apparatus into tissue or its movement through tissue (e.g., as a microcutter), can assist in the physical mixing of one or more compounds, can assist in the dispersion of compound to a target, or can skew or diminish the perception of pain when the apparatus is inserted into tissue.

In another embodiment, the ultrasound TCA apparatus 1000 can comprise a second cannula 60 for guiding the cannula (i.e., a "guide cannula").

In another embodiment, the ultrasound transducer 20 comprises a piezoelectric material 40. In embodiments comprising a plurality of ultrasound transducers, each transducer can comprise the same or different piezoelectric materials. The piezoelectric material can be any known in the art, e.g., piezoelectric ceramic, piezoelectric crystal, lead zirconate titanate (PZT) or polyvinylidene fluoride (PVDF). In a specific embodiment, the ceramic is a lead zirconate-titanate (PZT-4) ceramic.

The ultrasound transducer 20 comprising the piezoelectric material 40 can be used to produce an acoustic field. In certain embodiments, the ultrasound transducer comprising the piezoelectric material can be mounted on, or associated with, the cannula or another portion of the ultrasound TCA apparatus and can be used to detect and/or produce an acoustic field.

In another embodiment, the ultrasound transducer comprises electrodes, wherein the electrodes are operably connected to the ultrasound transducer and to the ultrasound driver (see Section 5.2).

In another embodiment, the ultrasound TCA apparatus comprises a stereotaxically controlled, robotically controlled or manual (e.g., hand-held) guide arm 200 for guiding the apparatus stereotactically, manually or robotically to a target.

In another embodiment, the ultrasound transducer can have portions defining a hole 70 (or canal or groove) for positioning of the cannula. The dimensions of these portions defining the hole 70 can be easily determined by the skilled practitioner. In a specific embodiment in which the ultrasound TCA apparatus has a single cannula, the ultrasound transducer can have a central hole or an offset hole. In another embodiment, the ultrasound transducer can have portions defining a plurality of holes, canals or grooves for positioning of a plurality of cannulas. In another specific embodiment, the ultrasound transducer can have a plurality of holes, canals or grooves for the positioning of a plurality of cannulas.

In another embodiment, a disposable cannula (e.g., needle, catheter, microcatheter, microfabricated catheter) is used, so that the cannula can be replaced and the apparatus employed in delivery of a compound to more than one patient or subject. In another embodiment, one or more cannulas can be preloaded with one or more compounds of interest to be infused to a target. Such preloaded and/or disposable cannulas can be used to deliver one or more compounds of interest to the target.

In another embodiment, the ultrasound TCA apparatus is an implantable apparatus.

In embodiments in which the ultrasound TCA apparatus comprises a plurality of ultrasound transducers, one transducer can produce a frequency of ultrasound that is the same as, or is different from, the frequency produced by another transducer. The frequencies can differ, for example, in their bioacoustical qualities, such as the ability to permeabilize a cell or tissue, or the ability of the acoustic energy produced to push or propel a compound to a desired target.

The frequency producing cell or tissue permeabilization can be, for example, from 20 kHz to 5 MHz.

Another bioacoustical quality is acoustic streaming quality. The frequency producing acoustic streaming can be, for example, from 500 kHz to 20 MHz.

In certain embodiments comprising a plurality of ultrasound transducers, the transducers can be positioned in an array on the cannula. In another embodiment, the plurality of ultrasound transducers can positioned in an array that is on (or distributed among) one or more cannulas in the plurality. The array can be, for example, a two-dimensional array (FIGS. 13A-B), a three-dimensional array, a semi-focused array or a plain array. The ultrasound transducer(s) or array of transducers can be positioned inside or outside of the cannula, and in certain embodiments, activation of the transducer(s) can cause the cannula to resonate or vibrate (FIGS. 15B and 15D).

In a specific embodiment, the ultrasound transducer can be positioned on an interface or connector for the cannula (FIGS. 15C-D). With an infusion needle, for example, the ultrasound transducer can be positioned on, near, or adjacent to a commercial connector such as a Luer-Lock connector. Such connectors are well known in the art. With such an arrangement the cannula of the ultrasound TCA apparatus can be made to vibrate, which can ease its insertion into the subject and guidance of it to the target. In other embodiments, as mentioned above, the ultrasound transducer can be positioned on the cannula itself. It will be apparent to the skilled practitioner that the vibration of the cannula can be regulated by positioning the ultrasound transducer(s) at different locations on the cannula.

In another embodiment, the ultrasound produced can be focused by beam steering.

In certain embodiments, the array of ultrasound transducers can be used for ultrasound imaging as well as for controlling distribution of the compound.

Various non-limiting embodiments of the arrangement of the ultrasound transducers and cannulas in the ultrasound TCA apparatus are provided herein.

FIG. 13A shows an embodiment of an ultrasound TCA comprising a plurality of ultrasound transducers 20 in a two-dimensional array. FIG. 13B shows a top view of the array of ultrasound transducers 20 in this embodiment.

FIG. 14A shows an embodiment in which a plurality of ultrasound transducers 20 is arranged in an array on a cannula 10. FIG. 14B shows a long, thin rectangular (strip) shaped ultrasound transducer 20 that can be mounted inside or outside of a cannula 10. FIG. 14C shows an embodiment of an ultrasound TCA comprising a plurality of ultrasound transducers 20 in a two-dimensional array. Additional ultrasound transducers 20 are positioned in arrays on two of the cannulas 10 (left and middle), from each of which a compound 900 is being infused.

FIG. 15B shows an embodiment in which two ultrasound transducers 20 are mounted on a cannula. The ultrasound produces a vibration in the cannula. FIG. 15C shows an embodiment of a TCA comprising two piezoelectric elements 40 mounted between a syringe connector 800 and a needle connector 820 (e.g., Luer-Lock) (Needle cannula 10; fluid port 850). FIG. 15D shows the embodiment of the TCA of FIG. 15C shown mounted on a syringe and vibrating the needle cannula.

The ultrasound TCA apparatus can comprise a housing for the ultrasound transducer. The housing is preferably a good acoustic material. Such materials are known in the art. The housing can be a biocompatible material and/or can be sterilizable, e.g., aluminum, titanium, stainless steel, acrylic, polystyrene (e.g., a cross-linked polystyrene microwave plastic such as REXOLITE®) or polyetherimide (PEI) thermoplastic (e.g., ULTEM®). All of these are known in the art as good acoustic materials and are Food and Drug Administration (FDA) approved. The housing can comprise a lens that can be used for controlling the shape of the ultrasonic field The lens can be concave, convex or flat to focus or broaden the ultrasound beam, as is known in the art. FIG. 15A shows concave, convex and flat housings 50 covering the piezoelectric material 40 in three embodiments of an ultrasound TCA. The different shapes of the housings can act as lenses to control or focus the ultrasound waves and acoustic fields produced.

Performance, e.g., ultrasonic intensity of the ultrasound TCA apparatus, can be characterized using methods known in the art, such as measuring the peak ultrasonic intensity of the acoustic field. Animal experiments can also be used to characterize the performance of the ultrasound TCA apparatus, e.g., delivery of a test compound. Further characterization of the performance of the ultrasound TCA apparatus can be accomplished using art-known image, statistical and/or histological analyses. See Section 6 for examples.

Ultrasound dosimetry can be determined for the ultrasound TCA apparatus. Mechanical index (MI) is a standard measure of the acoustic output in ultrasound systems, defined as the peak rarefactional pressure of an ultrasound longitudinal wave propagating in a uniform medium, divided by the square root of the center frequency of the transmitted ultrasound wave. According to the FDA guidelines for diagnostic obstetrics applications, the MI should not exceed 1.9, and for ophthalmic applications, the MI should not exceed 0.2 (AIUM. (1988). Bioeffects considerations for the safety of diagnostic ultrasound. *J Ultrasound Med.*, 7(9 Suppl), S1-S38; AIUM. (1993). *Bioeffects and safety of diagnostic ultrasound*. Laurel, Md.: American Institute of Ultrasound in Medicine; AIUM. (2000). *Mechanical bioeffects from diagnostic ultrasound: AIUM consensus statements*, 19, 67-170). To calculate the maximum MI achieved by the ultrasound TCA apparatus using S.I. units (f=1.34 MHz, I=950 W/m²), the intensity (I) and acoustic impedance of soft tissue (Z~1.6e6 kg/m²s) can be used (Schroeder, A. et al. (2009). Ultrasound, liposomes, and drug delivery: Principles for using ultrasound to control release of drugs from liposomes. *Chem. Phys. Lipids.* 162, 1-16) to calculate the pressure (P) and derive the following formula for the ultrasound TCA apparatus to calculate a MI according to:

$$MI = \frac{P}{\sqrt{f}} = \frac{\sqrt{I \cdot Z}}{\sqrt{f}} = \frac{\sqrt{950 \cdot 1.6e6}}{\sqrt{1.34}} \times 10^{-6} = 0.034 \quad (1)$$

Another standard measure that can be used to characterize the ultrasound TCA apparatus is the thermal Index (TI). TI is defined as the ratio of the emitted acoustic power to the power required to raise the temperature of tissue by 1° C. The TI is intended to indicate the likely temperature rise that might be produced after long exposure. A larger TI value represents a higher risk of damage due to temperature increases. For therapeutic applications, the FDA requires that TI's over 6 require further explanation and safety analysis. The calculated soft-tissue thermal index ($T_s$) using the ultrasound power (P) for the ultrasound TCA apparatus can be calculated by:

$$T_s = \frac{P \cdot f}{210} = \frac{(0.11)(1.34e3)}{210} = 0.638 \quad (2)$$

In other embodiments, magnetic resonance imaging (MRI), positron emission tomography (PET), computed axial tomography (CAT or CT scan) or multiphoton excited fluorescence (MPEF) microscopy, all techniques well known in the art, can be used to characterize performance of the ultrasound TCA apparatus. These techniques can also be used for monitoring the ultrasound TCA apparatus during use in a subject, as well as characterizing its performance prior to use in a subject.

5.2 Ultralow Output Impedance Ultrasound Driver

The ultrasound TCA apparatus comprises an ultralow output impedance ultrasound transistor based driver (also referred to herein as an ultralow output impedance ultrasound driver or driver circuit) that has the ability to apply a drive signal at a frequency corresponding to the ultrasound transducer's resonant frequency. The low output impedance of the driver circuit allows for a substantial portion of the energy to be delivered to the ultrasound transducer and converted to ultrasound energy. The power transfer efficiency of the circuit allows the ultrasound driver to be powered by a portable battery pack, while still delivering high ultrasound acoustic power. The ultrasound driver can provide energy in sufficient amounts making it suitable for a range of ultrasound driving applications including but not limited to therapeutic low and high power clinical systems, high intensity focused ultrasound HIFU, acoustical welding, industrial inspection, and other various forms of low-to-high power acoustic devices. The ultralow output impedance ultrasound driver produces an ultrasound drive signal waveform.

The ultrasound TCA apparatus can also comprise a connection between the ultrasound driver and the ultrasound transducer. The connection can be wired or wireless and can comprise a wired or wireless interface.

In one embodiment, the driver is a microprocessor-controlled ultralow output impedance ultrasound driver for ultrasound-assisted convection-enhanced delivery (UCED) comprising a printed circuit board (PCB) comprising a plurality of surface-mounted metal-oxide-semiconductor field-effect transistors (MOSFETs), wherein the MOSFETs are positioned in parallel or independent configuration, and wherein the MOSFETs drive a single piezoelectric transducer channel or multiple independent piezoelectric transducer channels. The driver can also comprise a MOSFET switching power supply.

The MOSFETs can be configured in a transistor-transistor logic (TTL) timing configuration to drive single or multiple independent channels. This configuration is described in WO2010/006293A9 entitled Ultrasound Wave Generating Apparatus by Lewis and Olbricht.

In a specific embodiment, the driver comprises a plurality of 16 MOSFETS.

In another embodiment, the driver is modified after the driver disclosed in WO2010/006293A9 entitled Ultrasound Wave Generating Apparatus by Lewis and Olbricht, which is incorporated herein by reference in its entirety. The MOSFETs of the driver are configured in a transistor-transistor logic (TTL) timing configuration to multiple (rather than single) independent channels.

FIG. 1C shows one embodiment of the ultrasound TCA apparatus 1000 showing the ultralow output impedance ultrasound driver and printed circuit board (PCB) 300 and the transducer cannula assembly (TCA) 100.

FIG. 16A is a schematic of an ultrasound TCA 100 with an array of n ultrasound transducers 20 in one row of an n×n two dimensional array. In FIG. 16B, each transducer in the array is operably connected to a single channel 310 ("c1," "c2," etc.) in the ultralow output impedance ultrasound driver 300.

In another embodiment, the driver can additionally comprise an onboard microprocessor controller for controlling ultrasound parameters. The microprocessor controller can control a single channel or multiple independent channels.

In another embodiment, the microprocessor controller measures ultrasound output energy.

In another embodiment, the driver comprises a waveform generator integrated circuit (IC) and the waveform generator IC is interfaced with the microprocessor controller, thereby creating a timing transducer or function generator.

In another embodiment, the driver additionally comprises a user interface and software for monitoring acoustic energy/ultrasound output energy, adjusting power, and/or modulating the ultrasound drive signal waveform.

In another embodiment, the driver has pulse width and drive signal frequency modulation of a TTL timing signal produced by the driver.

In another embodiment, the driver has real-time onboard electrical power output measurement from the driver.

In another embodiment, the driver has computer and/or onboard control of the MOSFET switching power supply.

In another embodiment, the driver comprises a driver overload monitor

In another embodiment, driver is battery powered, e.g., by lithium batteries.

In another embodiment, the ultrasound TCA apparatus comprises a user interface and software for monitoring acoustic energy produced by the ultrasound transducer, adjusting power produced by the ultrasound transducer, and/or modulating the ultrasound drive signal waveform.

The principles underlying the technology and construction of battery powered, pocket-sized ultrasound systems are known in the art (see, e.g., Lewis Jr., G. K., et al. (2008). Development of a portable therapeutic and high intensity ultrasound system of military, medical and research use. *Rev. Sci. Inst.,* 79, 1-9; Lewis Jr., et al. (2008). Development of a portable therapeutic ultrasound system for military, medical and research use. *J. Acoust. Soc. Am., POMA* 5, 122; Lewis Jr., G. K., et al. (2009). Wave Generating Apparatus, UPCT Patent Application No. PCT/US2009/50297; Henderson P., et al. (2010). A portable high intensity focused ultrasound device for the noninvasive treatment of varicose veins. *J. Vas. Surg.,* 51(3), 707-711; Lewis Jr. G K, et al. (2010). Design and characterization of a high-power ultrasound driver with ultralow-output impedance. *Rev. Sci. Inst.,* 80(11), 1-8). The ultralow output impedance ultrasound driver demonstrated in this example was based off of a 16-MOSFET, surface mount component, printed circuit board (PCB) design.

The construction of a specific embodiment of the ultralow output impedance ultrasound driver is described in Section 6.1., Example 1. An ultralow output impedance ultrasound driver was constructed on a double-sided PCB, which can be designed and created using PCB layout software (e.g., PCB123® Layout V2 software from Sunstone Circuits Inc.). The PCB had 16 N/P channel parallel MOSFETs in a transistor-transistor logic (TTL) timing configuration to provide efficient voltage transfer from the driver to the ultrasound transducer. The ultrasound driver had a 1.34 MHz crystal clock oscillator (ECS-100A-010, ECS Inc.) to time the driver at the resonance of the TCA. One or more rechargeable lithium ion battery packs could be wired in series and enclosed in an enclosure or housing. Power from the system was optionally made adjustable by switching between system battery packs to provide control of the clamped push-pull square wave drive signal.

5.3 Methods for Ultrasound-Assisted Convection-Enhanced Delivery (UCED) of Compound to a Target Using the Ultrasound TCA Apparatus A method is provided for ultrasound-assisted convection-enhanced delivery (UCED) of a compound to a targeted cell, tissue, or organ (hereinafter "target") in a subject. Any cell, tissue, organ or region of the body in a subject can be a target for UCED of a compound. In certain embodiments, the target is in a diseased state or subject to a medical disorder, e.g., cancer cells, tumors, etc.

In one embodiment, the method comprises the steps of:
providing an ultrasound transducer cannula assembly (TCA) apparatus;
contacting the ultrasound TCA apparatus to the target;
introducing the compound (or a solution thereof) into cannula;
activating the ultrasound transducer, thereby producing an acoustic field; and
releasing the compound from the cannula, whereby the compound contacts the target.

In one embodiment, the steps of activating the ultrasound transducer and releasing the compound are concurrent. In another embodiment, the step of activating the ultrasound transducer is after the step of releasing the compound. In another embodiment, the step of activating the ultrasound transducer is before the step of releasing the compound.

In another embodiment, the step of activating the ultrasound transducer and producing an acoustic field produces an acoustic field around, within, through or outside of the cannula.

The contacting step can comprise stereotactically, manually or robotically guiding the ultrasound TCA apparatus to the target. Methods for stereotactic guidance of cannulas are well known in the art. An acoustic field can be produced while the ultrasound TCA apparatus is being guided to the target, for example, to vibrate the cannula, which can diminish or skew the perception of pain or discomfort that may be caused by the introduction of the apparatus. The step of activating the ultrasound transducer to diminish or skew the subject's perception of pain can be before the step of contacting the ultrasound TCA apparatus to the target.

The compound to be delivered by the ultrasound TCA apparatus can be encapsulated. The step of activating the ultrasound transducer and producing an acoustic field can break the encapsulation and release the encapsulated compound.

The compound can be encapsulated by, for example, a lysosome, liposome, micelle, microbubble, or stabilized microbubble, or the compound can be (or be comprised in) a coated (e.g., polymer coated) nanoparticle.

Using the ultrasound TCA apparatus, a plurality of compounds can be delivered to the target. In certain embodiments, at least one member of the plurality of compounds is encapsulated. The step of activating the ultrasound transducer and producing an acoustic field can break the encapsulation and release the encapsulated compound. The released compound can then mix or associate with another member of the plurality of compounds.

In a specific embodiment, the activating step comprises adding stabilized microbubbles to the compound. For example, in an exemplary embodiment, $5 \times 10^5$ stabilized microbubbles per μl with median diameter of 2.5 μm (e.g., from Targestar™-P, Targeson Inc.) can be infused.

Microbubbles function as acoustic reflectors. Since air has high acoustic impedance, microbubbles can be used as ultrasound "contrast agents," and can be used in drug delivery because they are efficiently pushed by the ultrasound field. When microbubbles are combined with an infusate (e.g., a liquid composition comprising a drug to be delivered), the microbubbles behave like clouds that are pushed along with the compound in the acoustic field. Microbubbles make the acoustic field more effective by oscillating the tissue and helping to push drug further into the tissue.

Microbubble can also be propelled and made to behave like microbullets to "shoot" holes in tissue. Microbubbles can therefore be employed in transdermal drug delivery with the ultrasound TCA apparatus, as they can form cavitation bubbles, oscillate in an acoustic field at the skin surface, and make microperforations through tissue.

Stabilized microbubbles are preferable, as opposed to creating microbubbles with high powered ultrasound. The latter can injure tissue. Stabilized microbubbles can be infused along with a compound by applying a lower intensity acoustic field that does not injure tissue.

Preferably, the stabilized microbubbles have diameters that are smaller than the intercellular spaces among the cells in the tissues to which they are directed.

The compound can be infused through the ultrasound TCA apparatus using a standard microinfusion pump or external syringe pump and standard methods known in the art. In one embodiment, infusion and ultrasound therapy can be performed, e.g., with flow rates from 0.05 to 10 μl/min. Suitable flow rates can determined by art known methods and from guidelines well known in the art.

In another embodiment, because ultrasound can be used in continuous wave mode for ultrasound-assisted CED (UCED), standing waves or focused fields can be induced in target cells, tissues, or organs, e.g., for generating a desired patterns of compound(s) that are infused to target cells, tissues or organs. Section 6.2, Example 2, describes an example of creating standing waves in a target tissue using the ultrasound TCA device. Standing waveform or focused field can also be used to surround, confine or move delivered compound(s) to a desired location in the tissue or organ in which the ultrasound TCA apparatus is deployed.

Acoustic pressure produced by the ultrasound TCA apparatus can be used to create high pressure areas to prevent diffusion of a compound past a desired location. The acoustic focus can be manipulated or steered to control the infusion of a compound to a target. A compound can also be released to a target, and then release can be followed by production of ultrasound to control diffusion of the compound to the target.

5.4 Method for Making Ultrasound Transducer Cannula Assembly (TCA) Apparatus

A method for making an ultrasound transducer cannula assembly (TCA) apparatus is also provided. FIG. 1A shows one embodiment of a method for making the ultrasound TCA apparatus.

The method can comprise the steps of:

providing a cannula, a piezoelectric material with two electrically conducting surfaces, an electrical conductor, and a housing with a transducer face;

fashioning an ultrasound transducer from the piezoelectric material, wherein the ultrasound transducer comprises portions defining a hole, canal or groove for positioning of the cannula;

attaching the electrical conductor to the ultrasound transducer face, wherein the electrical conductor is electrically isolated from one of the two conducting surfaces of the piezoelectric material;

positioning the ultrasound transducer within the housing;

positioning the cannula through the positioning hole, canal or groove; and attaching the cannula to the ultrasound transducer.

Referring to FIG. 1A, the ultrasound transducer cannula assembly (TCA) apparatus 1000 can be made by providing a piezoelectric material 40 and cutting an ultrasound transducer 20 from the piezoelectric material having a center hole to a desired size ("cutout disk" in FIG. 1A).

The piezoelectric material typically has an electrically conductive coating, e.g., a metal coating on its two outer surfaces (e.g., its front and back surfaces).

An electrical conductor 30 can be provided, wherein the electrical conductor can, in some embodiments, also function as a guide for the cannula or needle 60 (also referred to herein as "guide cannula" or "needle guide"). In other embodiments, the electrical conductor and the guide cannula can be separate components. In embodiments with multiple cannulas, multiple guide cannulas can be used.

In the embodiment shown in FIG. 1A, the electrical conductor 30 is inserted into the center hole 70 of the ultrasound transducer 20 and the electrical conductor is attached to the face (housing 50) of the ultrasound transducer. The electrical conductor can be made of brass (as is shown in FIG. 1A) or any other good electrical conductor known in the art (e.g., metals such as silver, gold, etc.).

FIG. 1B shows a close up photograph of an embodiment of the ultrasound transducer 20, showing the piezoelectric material 40 (in this embodiment, a piezoelectric ceramic disk) and the electrical conductor 30 (also the guide cannula or needle guide in this embodiment), mounted on a standoff on the housing 50 (in this embodiment, an aluminum standoff and housing.)

One of the conductive surfaces of the piezoelectric material of the ultrasound transducer is electrically isolated from the electrical conductor. In one embodiment, the positive electrical connection is on the back surface of the piezoelectric material of the ultrasound transducer and the negative connection is on the front surface. In some embodiments, the electrical conductor goes through the piezoelectric material and makes an electrical connection with the front conductive surface of the piezoelectric material, while maintaining electrical isolation from the back conductive surface of the piezoelectric material. In other embodiments, the transducer face or housing (e.g., an aluminum standoff) is the electrical connection to the front conductive surface of the piezoelectric material.

A housing 50 can be provided and the ultrasound transducer 20 can be positioned in the housing. The housing can be made of any suitable material known in the art, e.g., plastic, aluminum or a combination of suitable materials. The housing 50, within which is positioned the ultrasound transducer 20, can be assembled so that it is operably associated with a guide arm 200 (e.g., stereotaxic, manual or robotic guide arm).

A cannula 10 for infusion, such as a needle, catheter or miocrocatheter and/or a second cannula for guiding the cannula ("guide cannula") can be inserted into the housing 50, as shown in FIG. 1A.

Connecting cables or wires (e.g., coaxial cables) can be attached to the transducer positioned in the housing that is assembled with the stereotaxic guide arm.

The construction of the ultrasound TCA apparatus is preferably accomplished using multiple iterations and careful machining, using art-known methods, because of the fragility of the piezoelectric material (e.g., ceramic). Soldering and final wire connections are preferably completed under a stereoscope.

It will be apparent to the skilled practitioner that the manufacturing steps above can be varied so that the cannula 10 and ultrasound transducer 20 can be manufactured as a single component.

5.5 Uses of the Ultrasound TCA Apparatus

The ultrasound TCA apparatus can be used anywhere in the body for delivery of a desired compound to a target cell, tissue or organ. The apparatus can be used to deliver a desired compound e.g., subcutaneously, to tumors, or to teeth or gums in dentistry.

The ultrasound TCA apparatus can be used to reduce backflow, increase the penetration distance and provide control over the spatial distribution of the delivery of an infused compound to a target cell, tissue or organ of interest.

The ultrasound TCA apparatus can be used to improve the spatial distribution of compound delivered directly to the target, typically by four to six times over cannula enhanced delivery (CED), without causing any additional damage to the target. In addition, the use of ultrasound can allow for more concentrated delivery of a compound and thus uses less of the compound than non-ultrasound methods.

The ultrasound TCA apparatus can be used for treatment of difficult-to-cure diseases, such as certain cancers and tumors (e.g., glioblastoma multiforme of the brain), in which the majority of tumor is typically removed, but not the margins. The ultrasound TCA apparatus can be used in the delivery and focusing of compounds against those remaining cells to help prevent the recurrence of the disease. An additional benefit is that since the targeting can be more focused, less compound is needed, thus a lower potential for harmful effects to the host and host cells.

The ultrasound produced by the ultrasound TCA apparatus can also be employed to diminish or skew the perception of pain as the apparatus is introduced into the vicinity of a target.

The ultrasound TCA apparatus can be used to produce a standing wave or acoustic field. Because ultrasound can be used in continuous wave mode for ultrasound-assisted CED (UCED), standing waves can be induced in target cells, tissues or organs, e.g., for generating banding patterns of tracer compounds that are infused to target cells, tissues or organs. Low-intensity ultrasound can thus be used for additional drug delivery applications beyond improving the distribution of pharmaceuticals in the brain. For example, various standing wave patterns can be induced during an infusion to provide greater spatial and temporal control over the infusion. Such control is valuable with highly toxic treatments.

Inducing a standing wave depends on correct alignment in the desired geometry as well as the correct ultrasound frequency. Inducing such a standing wave field in vivo preferably uses real-time imaging and precise positioning of the ultrasound source. However, if standing waves are determined to prove harmful to the targeted tissue, measures can be taken to prevent their formation, such as randomizing frequency or moving the source (Tang, S. C., et al. (2010) Standing wave suppression for transracial ultrasound by random modulation. *IEEE Trans Biomed Eng.* 57 203-5). Ultrasound can directly affect the distribution profile of an infusate during CED and parameters governing UCED can be optimized, using standard methods known in the art, to provide clinically relevant therapy for diseases or disorders.

The following examples are offered by way of illustration and not by way of limitation.

6. EXAMPLES

6.1 Example 1: Ultrasound Assisted Convection Enhanced Drug Delivery to the Brain In Vivo with a Transducer Cannula Assembly

6.1.1 Introduction

In traditional convection enhanced delivery (CED), drugs are infused locally into tissue through a cannula inserted into brain parenchyma. Transport of the infused material is dominated by convection, which enhances drug penetration into tissue compared with diffusion mediated delivery. Ultrasound has been shown to assist and/or mediate the delivery of pharmaceuticals across membranes and through tissues. This example demonstrates ultrasound-assisted convection enhanced delivery (UCED) of a test compound (Evans blue dye) to the rat brain in vivo using a low profile transducer cannula assembly (TCA) and portable and pocket-sized ultrasound system, referred to herein as a ultrasound transducer cannula assembly (TCA) apparatus.

A total of 40 Sprague-Dawley rats (350 to 450 g) were divided into two equal groups and further divided into four equal subgroups (n=5 in each). The rats were anesthetized, secured into ear bars on a stereotaxic apparatus, and a craniotomy was performed. The caudate of the rat brain was infused with 0.25 wt % Evans blue dye (EBD) in Phosphate-Buffered Saline (PBS) at two different infusion rates of 0.25 μL/min for group 1, and 0.5 μL/min for group 2. Infusion flow rate was slowly increased over 10 minutes from 0.05 to 0.25 μl/min for group 1 n=20 rodents and 0.1 to 0.5 μl/min for group 2 n=20 rats, and maintained at the final flow rate for 20 min thereafter, for a total experiment duration of 30 min in both groups. Using the TCA without ultrasound, the four control subgroups were infused without and with microbubbles (CED and CED+MB). The four UCED subgroups (UCED and UCED+MB) followed the same protocol with the addition of simultaneous continuous wave 1.34 MHz ultrasound operating at a total acoustic power of 0.11+/−0.005 W and peak spatial intensity at the cannula tip of I=49.7 $mW/cm^2$. Frozen sectioning and histology were performed on the brains, and infusion distribution was three-dimensionally reconstructed using MatLab® analysis. Hematoxylin and Eosin (H&E) staining was used to assess tissue damage and morphological changes to the brain. The application of UCED and UCED+MB improved EBD total volumetric distribution by 2.24 to 3.25 and 1.16 to 1.70 times, respectively (p<0.001). On gross and histological examination, no ultrasound or microbubble related damage to the brain tissue was found. The TCA and battery-powered ultrasound device show promise to improve the distribution of infusate during CED in clinical practice.

6.1.2 Background

Convection enhanced delivery (CED) uses direct infusion of therapeutics into the brain to bypass the blood-brain barrier (Bobo, R. H. et al. (1994). Convection-enhanced delivery of macromolecules in the brain. *Proc. Natl. Acad. Sci. USA*, 91, 2076-2080). The infusion takes place through a cannula that is inserted directly into brain parenchyma. The infusion establishes a pressure gradient in the tissue that causes material to flow outward from the needle tip. Small molecules such as sucrose can be transported effectively by convection. However, larger molecules such as proteins may interact with components of the extracellular matrix (ECM) and with cell membranes, which can inhibit their transport. Furthermore, many therapeutics of clinical interest are subject to elimination by several mechanisms, including clearance into capillaries, binding to cell membranes, internalization into cells, and enzymatic metabolism. The distance that a therapeutic penetrates into the brain and its concentration profile in the interstitium depend on relative rates of convection and elimination. In principle, increasing the infusion rate can increase the rate of convection and thereby increase the distance that infused molecules penetrate at therapeutically useful concentrations. However, brain tissue is poroelastic, and it deforms in response to the local pressure associated with the infusion. For sufficiently high infusion rates, the tissue separates from the outer surface of the infusion needle, which opens a gap allowing infused material to escape the parenchyma (Chen, M. Y. et al. (1999). Variables affecting convection enhanced delivery to the striatum: a systematic examination of rate of infusion, cannula size, infusate concentration, and tissue-cannula sealing time, *J. Neurosurg.* 90, 315-320; Morrison, P. F., et al. (1999). Focal delivery during direct infusion to brain: role of flow rate, catheter diameter, and tissue mechanics. *Am. J. Physiol. Regul. Integr. Comp. Physiol.* 277, R1218-R1229, 1580-1596). Although judicious catheter designs can reduce this effect, backflow along the outside of the needle sets an upper limit on the infusion rate, which, in turn, sets an upper bounds on the convection rate and penetration distance in the parenchyma.

Extending the penetration distance in CED is essential for the treatment of glioblastoma multiforme (GBM), a high-grade glioma that is usually treated with tumor resection, external beam irradiation and chemotherapy. However, GBM characteristically has diffuse boundaries, and invariably malignant cells have migrated away from the main tumor prior to resection, thus limiting the impact of surgery. Traditional chemotherapy and radiation therapy administered post-resection are unable to eliminate all of the remaining malignant cells. As a result, the malignancy recurs, usually within 1 cm of the original tumor. Median survival is approximately one year after the diagnosis of GBM (Rainov, N. G., et al. (2006). Novel therapies for malignant gliomas: a local affair? *Neurosurg. Focus*, 20, E9). CED has been used in animal studies to infuse small molecules (Bobo, R. H., et al. (1994). Convection-enhanced delivery of macromolecules in the brain. *Proc. Natl. Acad. Sci. USA*, 91, 2076-2080; Lonser, R. R., et al. (1999). Convection-enhanced selective excitotoxic ablation of the neurons of the globus pallidus internus for treatment of parkinsonism in nonhuman primates. *J. Neurosurg.*, 91, 294-302; Groothuis, D. R., et al. (1999). Comparison of c-14-sucrose delivery to the brain by intravenous, intraventricular, and convection-enhanced intracerebral infusion. *J. Neurosurg.*, 90, 321-331), proteins (Lieberman, D. M., et al. (1995). Convection-enhanced distribution of large molecules in gray matter during interstitial drug infusion. *J. Neurosurg.*, 82, 1021-1029), growth factors (Hamilton, J. F., et al. (2001). Heparin coinfusion during convection-enhanced delivery (ced) increases the distribution of the glial-derived neurotrophic factor (gdnf) ligand family in rat striatum and enhances the pharmacological activity of neurturin. *Exp. Neurol.*, 168, 155-161), nucleotides (Broaddus, W. C., et al. (1998). Distribution and stability of antisense phosphorothioate oligonucleosides in rodent brain following direct intraparenchymal controlled-rate infusion. *J. Neurosurg.* 88, 734-742), liposomes and polymeric nanoparticles for therapeutic and imaging purposes (Yamashita, Y., et al. (2007). Convection-enhanced delivery of a topoisomerase I inhibitor (nanoliposomal topotecan) and a topoisomerase II inhibitor (pegylated liposomal doxorubicin) in intracranial brain tumor xenografts. *Neuro-oncol.*, 9, 20-28; Neeves, K. B., et al. (2007). Dilation and degradation of the brain extracellular matrix enhances penetration of infused polymer. *Brain Res.*, 1180, 121-132). Chemotherapy agents (Mardor, Y., et al. (2001). Monitoring response to convection-enhanced taxol delivery in brain tumor patients using diffusion-weighted magnetic resonance imaging. *Cancer Res.*, 61, 4971-4973), viral vectors (Ren, H., et al. (2003). Immunogene therapy of recurrent glioblastoma multiforme with a liposomally encapsulated replication-incompetent semliki forest virus vector carrying the human interleukin-12 gene a phase i/ii clinical protocol. *J. Neuro-Oncol.* 64, 147-154), and proteins (Sampson, J. H., et al. (2003). Progress report of a phase i study of the intracerebral microinfusion of a recombinant chimeric protein composed of transforming growth factor (tgf)-α and a mutated form of the Pseudomonas exotoxin termed pe-38 (tp-38) for the treatment of malignant brain tumors. *J. Neuro-Oncol.*, 65, 27-35) have been infused into humans in clinical trials. The results of these studies are highly variable, but some have shown that infused therapeutics can penetrate deep into the brains of small animals with tumor xenografts, and these studies often show corresponding decreases in mortality. In human trials, however, delivery of the drug to malignant cells remains a major challenge for CED (Weber, F., et al. (2003). Safety, tolerability, and tumor response of i14-Pseudomonas exotoxin (nbi-3001) in patients with recurrent malignant glioma. *J. Neuro-Oncol.*, 64, 125-137; Kunwar, S., et al. (2007). Direct intracerebral delivery of cintredekin besudotox (IL13-PE38QQR) in recurrent malignant glioma: a report by the Cintredekin Besudotox Intraparenchymal Study Group. *J. Clin. Oncol.*, 25, 837-844), as described in recent reviews (Vogelbaum, M. A. (2007). Convection enhanced delivery for treating brain tumors and selected neurological disorders: symposium review. *J. Neuro-Oncol.*, 83, 97-109; Lopez, K. A., et al. (2006). Convection-enhanced delivery in the treatment of malignant glioma. *Neurol. Res.*, 28, 542-548; Huynh, G. H., et al. (2006). Barriers to carrier mediated drug and gene delivery to brain tumors. *J. Control Release.*, 110, 236-259).

The use of ultrasound to enhance drug delivery has evolved over several decades. Perhaps the most extensively studied example is the use of ultrasound to enhance transdermal drug delivery (Mitragotri, S., et al. (1995). Ultrasound-mediated transdermal protein delivery. *Science*, 269, 850-853; Boucaud, A., et al. (2002). Effect of sonication parameters on transdermal delivery of insulin to hairless rats. *J. Pharm., Sci.* 91, 113-119; Machet, L., et al. (2002). Phonophoresis: efficiency, mechanisms and skin tolerance. *Int. J. Pharm.,* 243, 1-15; Smith, N. B., et al. (2003). Ultrasound-mediated transdermal in vivo transport of insulin with low-profile cymbal arrays. *J. Ultrasound Med. Bio.,* 29, 1205-1210). Exposure of skin to ultrasound over a wide range of frequencies increases the permeability of the stratum corneum, allowing transport across skin of some therapeutic compounds that would otherwise be excluded and enhancing transport rates of others. Although a variety of thermal and non-thermal mechanisms could be important, investigators who have studied the effect of ultrasound parameters on transport enhancement concur that the underlying mechanism is acoustic cavitation (Guzman, H. R., et al. (2002). Equilibrium loading of cells with macromolecules by ultrasound: Effects of molecular size and acoustic energy. *J. Pharm. Sci.,* 91, 1693-1701; Keyhani, K., et al. (2001). Intracellular drug delivery using low-frequency ultrasound: Quantification of molecular uptake and cell viability. *Pharm. Res.,* 18, 1514-1520). Large pressure forces generated during the collapse of cavitation bubbles disrupt the adjacent stratum corneum, opening paths to underlying tissue and capillaries. At lower power levels, ultrasound can generate acoustic streaming, which is a local convective motion of liquid due to oscillating bubbles. If the liquid contains a concentration gradient of a solute, acoustic streaming can enhance mass transfer of the solute without inducing a significant bulk motion of the liquid.

Recently, high intensity focused ultrasound (HIFU) has been shown to be an effective tool to target systemic drug treatments (Patrick, J. T., et al. (1990). Ultrasound and the blood brain barrier. *Adv. Exp. Med. Biol.,* 267, 369-381; Hynynen, K., et al. (2007). Clinical applications of focused ultrasound—The brain. *Int. J. Hyperth.,* 23, 193-202). Ultrasound mediated disruption of the blood brain barrier is being studied to help drugs escape the blood stream and enter the brain (Hynynen, K. et al. (2007). Clinical applications of focused ultrasound—The brain. *Int. J. Hyperth.,* 23, 193-202). Ultrasound has also been shown to enhance the convective transport of molecules in agarose, muscle and brain tissue in vitro (Lewis, G. K., et al. (2007). A phantom feasibility study of acoustic enhanced drug perfusion in neurological tissue. *Proc. IEEE, LISA,* 67-70; Lewis, Jr. G. K., et al. (2007). Acoustic targeted chemotherapy in neurological tissue. *J. Acoust. Soc. Am.,* 122, 3007; Lewis Jr., G. K., et al. (2008). Therapeutic ultrasound enhancement of drug delivery to soft tissues. *8th. Int. Sym. Ther. Ultrasound, AIP conf Proc.,* 1113, 403-407).

This example demonstrates that ultrasound may be applied in conjunction with CED to enhance the penetration of small molecules in the caudate of the rat brain. This may be done with a 0.64 cm diameter 1.34 MHz transducer cannula assembly (TCA), powered by an ultralow-output impedance hand-held ultrasound generating device that costs under $200.00 in parts (Lewis Jr., et al. (2008). Development of a portable therapeutic and high intensity ultrasound system of military, medical and research use. *Rev. Sci. Inst.,* 79, 1-9; Lewis Jr., G. K., et al. (2008). Development of a portable therapeutic ultrasound system for military, medical and research use. *J. Acoust. Soc. Am., POMA* 5, 122; Lewis Jr. G K, et al. (2010). Design and characterization of a high-power ultrasound driver with ultralow-output impedance. *Rev. Sci. Inst.,* 80(11), 1-8). The results suggest that ultrasound may also improve the distribution volume for other catheter designs known in the art. The ability of ultrasound to improve CED, and the portability and low-cost of the ultrasound generating technology, demonstrates its suitability for many medical applications.

6.1.3 Materials and Methods

Making the Ultrasound Transducer Cannula Assembly (TCA)

This section describes a method for making one embodiment of the ultrasound transducer cannula assembly (TCA) portion of the ultrasound TCA apparatus. This embodiment comprised three main parts: 1. A cylindrical lead zirconate-titanate (PZT-4) ceramic, 2. A 30 gauge infusion needle and 3. A stereotaxic guide arm for precision alignment. The TCA functioned as an axial resonating device that provided a cylindrical therapeutic acoustic field around the infusion needle during stereotaxic guided CED treatment.

FIG. 1A shows one embodiment of a method for making the TCA. A 3×3 cm sheet of polarized 1.34 MHz PZT-4 (EBL-4, EBL Products Inc.) with gold electrodes was machined into a cylinder with diameter of 0.64 cm using a CNC milling machine (5400, Sherline Products Inc.) and general diamond tipped bore. The center of the cylindrical ceramic was found, and a precision diamond grinding point (4376A11, McMaster-Carr Inc.) was used to grind a 0.08 cm diameter hole through the center. All of the ceramic machining was conducted under a water bath to prevent toxic dust particles and remove heat generated from tooling process. The grinding point was also used to remove gold conductor from the top (inside) surface around the hole in the ceramic to electrically isolate the brass tube from the top surface.

The brass tube was flanged and inserted through the hole in the ceramic, and connected to the front face (bottom surface) with solder. The ceramic with brass tube was then placed in a low-profile PVC/aluminum assembly (Air-backed) with a stereotaxic guide arm as shown. The brass tube (electrical-ground) and top surface (electrical-hot) of the ceramic were wired through the stereotaxic guide arm with 5Ω coax-cable (NMEF 1/22-15044 SJ, Cooner Wire Inc.). A 30 gauge cannula-guide and 11 mm infusion cannula (8IC317I and 8IC317G, Plastics One Inc.) were mounted onto the assembly and affixed to the housing with 5-minute epoxy. The infusion cannula was positioned through the center of the assembly and perpendicular to the face of the transducer, to allow 5 mm of length from the face of the transducer to the cannula's tip. The electrical impedance of the transducer cannula assembly (TCA) was measured using commonly known methods, to determine the resonant frequency for efficient ultrasound generation (Lewis Jr., et al. (2008). Cost effective broad-band electrical impedance spectroscopy measurement circuit and signal analysis of piezo-materials and ultrasound transducers. *Meas. Sci. Technol.,* 19, 1-7).

Making the Pocket-Sized Ultrasound System

The principles underlying the technology and construction of battery powered, pocket-sized ultrasound systems are well known in the art (see, e.g., Lewis Jr., G. K., et al. (2008). Development of a portable therapeutic and high intensity ultrasound system of military, medical and research use. *Rev. Sci. Inst.,* 79, 1-9; Lewis Jr., et al. (2008). Development of a portable therapeutic ultrasound system for military, medical and research use. *J. Acoust. Soc. Am., POMA* 5, 122; Lewis Jr., G. K., et al. (2009). Wave Generating Apparatus, UPCT Patent Application No. PCT/US2009/50297; Henderson P., et al. (2010). A portable high intensity focused ultrasound device for the noninvasive treatment of varicose veins. *J. Vas. Surg.,* 51(3), 707-711; Lewis Jr. G K, et al. (2010). Design and characterization of a high-power ultrasound driver with ultralow-output impedance. *Rev. Sci. Inst.,* 80(11), 1-8). The ultralow output impedance ultrasound driver demonstrated in this example was based off of a 16-MOSFET, surface mount component, printed circuit board (PCB) design.

The ultralow output impedance ultrasound driver was constructed on a double-sided PCB, which was designed and created using PCB123® Layout V2 software from Sunstone Circuits Inc. The 3.8×7.62 cm PCB has 16 N/P channel parallel MOSFETs in a transistor-transistor logic (TTL) timing configuration to provide efficient voltage transfer from the driver to the ultrasound transducer. The ultrasound driver, 1.34 MHz crystal clock oscillator (ECS-100A-010, ECS Inc.) to time the driver at the resonance of the TCA, and three 7.4 V 2400 mAh rechargeable lithium ion battery packs (18650, Portable Power Inc.) wired in series are all enclosed in an ergonomic 12.2×7.9×3.3 cm plastic enclosure (PPLX, PacTec Inc). Power from the system can be optionally made adjustable by switching between system battery packs to provide control of the clamped push-pull square wave drive signal between +/−7.4 or +/−11.1 V. For the purpose of this example, the system was used at +/−11.1 V setting because of the high electrical impedance of the TCA. See also Lewis and Olbricht (WO2010/006293A9, entitled Ultrasound Wave Generating Apparatus, PCT/US2009/050297) for methods of construction of ultralow output impedance ultrasound drivers.

Characterizing the Ultrasound TCA Apparatus with Ultrasound Exposimetry

Ultrasonic intensity of the ultrasound TCA apparatus was characterized using methods known in the art. The peak ultrasonic intensity of the acoustic field was measured with an omnidirectional reference hydrophone (HNR 1000, calibrated Jul. 12, 2010, Onda Inc.) in parallel planes 0.25 mm from the TCA's face and at the cannula tip (5 mm from the TCA face). The TCA was submerged in a distilled and degassed (2 ppm) water tank (30×30×85 cm in size) that was made almost completely anechoic by placing a 1.27 cm thick wall of sound absorbing rubber around its wall (8456K417, McMaster-Carr Inc).

Precise, micromanipulator-controlled positioning of the hydrophone was performed by hand using micro milling machine (5400, Sherline Products Inc.). Ultrasonic waves detected by the hydrophone were recorded by measured voltages using a digitizing oscilloscope (TDS2002B, Techtronix Inc.) and converted into intensity measurements using a calibration table provided by Onda Inc. The scanning step size for each plane was 1 mm and the scanning area was 10×10 mm. Spatial peak-temporal peak-intensity were determined for each plane by scanning with the hydrophone in 1 mm increments and averaging over 3 measurements (IEEE. (1990). *Guide for medical ultrasound field parameter measurements*. New York: Institute of Electrical and Electronics Engineers, Inc.; AIUM. (1998). *Acoustic output labeling standard for diagnostic ultrasound equipment*. Laurel, Md.: American Institute of Ultrasound in Medicine). The total acoustic power was measured with a radiation force balance system (RFB 2000, Onda Inc.) using a rubber disk absorbing target (RFB CTK, Onda Inc.) in distilled and degassed water. Results were compared with electrical measurements of intensity and power using the electrical properties of the TCA and measured ultrasonic power conversion efficiency from the Mason transmission line model (Lewis Jr., et al. (2008). Development of a portable therapeutic and high intensity ultrasound system of military, medical and research use. *Rev. Sci. Inst.*, 79, 1-9; Lewis Jr., et al. (2008). Development of a portable therapeutic ultrasound system for military, medical and research use. *J. Acoust. Soc. Am., POMA* 5, 122; Lewis Jr. G K, et al. (2010). Design and characterization of a high-power ultrasound driver with ultralow-output impedance. *Rev. Sci. Inst.*, 80(11), 1-8).

Characterizing the Ultrasound TCA Apparatus in Animal Experiments

FIG. 2 shows the animal experimental setup for testing the ultrasound TCA apparatus in the rat brain. Rats were anesthetized and euthanized by procedures approved by the Institutional Animal Care and Use Committee (IACUC) at Cornell University. A total of 40 Sprague-Dawley rats (350 to 450 g) were divided into two groups (designated Groups 1 and 2) with four subgroups (5 rats in each subgroup). Animals were anesthetized by inhalation of isoflurane gas and secured in a stereotaxic frame. The head was shaved, 0.5 ml of bupivicaine was applied under the skin as a local anesthetic and an incision was made in the skin along the dorsal midline of the skull. A small craniotomy (6-7 mm diameter) was made over the left side of the exposed skull using a dental drill. The TCA was guided using a micromanipulator to +0 mm anterior, +3 mm lateral and −5.5 mm ventral from bregma, lowered at 0.25 mm per second into the caudate of the rat brain and allowed to equilibrate for two minutes. 1-2 ml of artificial cerebral spinal fluid (aCSF) and a gel-foam dam was used to couple acoustic energy from the face of the TCA into the rodent brain. The TCA was powered on with the pocket-sized ultrasound system at the +/−11.1 V setting and infusion began.

For each rat, the entire experiment lasted a total of 30 min. The control subgroups of CED and CED+MB (n=5 in each) were infused using the TCA with no ultrasound therapy for 30 min. For the experimental subgroups of UCED and UCED+MB (n=5 in each), infusion and ultrasound exposure at an acoustic power of 0.11+/−0.005 W, and TCA face intensity of 0.095 W/cm$^2$ which corresponded to a cannula tip intensity of 0.0497 W/cm$^2$ for 30 min was applied simultaneously. Filtered Evan's blue dye (EBD) 0.25 wt % in phosphate buffered saline (PBS) without or with 5×10$^5$ stabilized microbubbles per μL with median diameter of 2.5 μm (Targestar™-P, Targeson Inc.) was infused using a microinfusion pump (Worker Bee™, Bioanalytical Systems, Inc.).

The starting infusion flow rate for the experiments of Group 1 was 0.05 μL/min for 5 min; the infusion flow rate was then increased to 0.1 μL/min for an additional 5 min, to a final flow rate of 0.25 μL/min for 20 min. The starting infusion flow rate of Group 2 was 0.1 μL/min for 5 min; the infusion flow rate was then increased to 0.25 μL/min for an additional 5 min, to a final flow rate of 0.5 μL/min for 20 min.

After 30 min of simultaneous infusion and ultrasound therapy the experiment was stopped. The TCA was left in the tissue for 1-2 min before being removed while euthanasia via cardiac urethane injection was performed. The animal was removed from the stereotaxic frame and immediately perfused with 200 mL of PBS followed by 200 mL 4% paraformaldehyde fix. The brain was then promptly removed from the skull using bone cutters and prepared for frozen section in 30% sucrose and 4% paraformaldehyde solution for one day, and moved to 60% sucrose and 4% paraformaldehyde solution for another day, before being frozen on dry ice in optimal cutting temperature (OCT) embedding.

Characterizing the Ultrasound TCA Apparatus Performance Using Image, Statistical and Histological Analyses Tissue slices were imaged using a CCD camera (Canon Power Shot G10, Canon Inc.) arranged on a cryostat (Microm HM 550, Thermo Scientific) during frozen section through the brain in the coronal plane. The high resolution 14 Mpix Joint Photographic Experts Group (JPEG) image files were captured at the first visualization of EBD in the brain tissue and after every fifth 50 μm brain slice until EBD was no longer distinguishable. The digital image files were cropped to include the rodent brain with a white ring of OCT embedding around its outside and resized to 100×70 pixels with a locked aspect ratio using ADOBE® PHOTOSHOP® ("Adobe Photoshop," Adobe Systems, Inc.) for further analysis in MATLAB® ("MatLab," Mathworks Inc.).

Each coronal brain section was loaded into MatLab using the imread( ) function and the pixel to physical length ratio was determined using a calibration ruler measure taken in the picture frame windows. The imread( ) function returned a 100×70×3 unit8 matrix of Red Green Blue (RGB) 24-bit color intensity data for each pixel in each frame. RGB pixel values making up the white ring of OCT imbedding around the brain tissue section were used to adjust for slight lighting variations between image frames and samples studied. The white OCT RGB pixel values were measured in the top, bottom, left and right quadrants of the image frames, averaged, and used to determine a weighting factor. Across samples on average, the standard white OCT pixels of the data sets had RGB values of Red=171, Green=175 and Blue=177, respectively. These standard OCT values were used to determine each channel's color intensity waiting factor per image frame. Each RGB waiting factor was then applied across the 100×70×3 unit8 matrix of RGB data frames. For volume distribution analysis of EBD in the brain section the Red, Green and Blue intensity values that composed each pixel were added algebraically with additional weight placed on the Blue channel (Red channel+Green channel+2× Blue channel) to generate a 100×70×1 summed color intensity matrix. A threshold value of 260 intensity counts was experimentally determined to best include all of the EBD pigment image data and was applied across the summed color intensity matrix where any matrix component over 260 was set to 0. The final intensity matrix for each picture frame consisted of 100×70 matrix values ranging from 0-260, with 1 being the darkest pigment, 260 being the lightest pigment and 0 acting as an empty matrix space holding component. EBD distribution area in each picture frame was measured by whether or not each pixel in the 100×70 matrix picture frame held a value greater than 0. The EBD volume distribution represented by each brain section was calculated by multiplying each frames distribution area by 5×50 μm, for a total slice width of 250 μm (to account for all sections each individual slice represented). Each analyzed image section was then placed into a 3D-stack and summed as a whole to obtain the total brain distribution volume of EBD. The 3D stack was additionally compiled using the contourslice( ) and isosurface( ) functions in MatLab to generate a 3D visualization of each data set and to display the total infusion distribution volume in the rodent brain. The left hemisphere and the left caudate of each rat brain were analyzed separately to compare EBD distribution in the two regions. In analysis of the left caudate, the 100×70 pixel image frames of each data set were cropped in Adobe Photoshop to include only the gray matter track of the caudate region, and then reanalyzed as before.

Standard statistical analyses were performed using MatLab. An ANOVA was used to analyze the statistical significance of the total infusion distribution volumes in the four control and four experiential subgroups. The statistical tests compared if the means from the groups were equal, against the alternative that the means were not equal. The p-value was used to determine if the difference between groups was significantly greater then chance.

Standard methods of histological examination were used to determine any acute and morphological changes due to ultrasound-assisted CED. Fixed brain tissue samples from rodents undergoing CED, CED+MB, UCED and UCED+MB infusions were delivered to the Cornell University Veterinary Pathology Department and 10 μm coronal sections at the cannula insertion plane and were collected using the paraffin method, and saved on microscope slides for histology. Standard histological analysis was conducted by hematoxylin and eosin (H&E) staining of 10 μm sections by the Cornell University Veterinary Pathology Department. An independent review was obtained from the Pathology Department at Cornell University to determine if any difference between subgroups was found.

6.1.4 Results

Characteristics of Transducer Cannula Assembly and Ultrasound System

The construction of the TCA required multiple iterations and careful machining because of the fragility of the ceramic. Soldering and final wire connections were completed under stereoscope. The electrical impedance magnitude of the TCA is shown in FIG. 3. The TCA resonates at 1.18 MHz with a 380Ω electrical impedance and antiresonance at 3.1 MHz. The phase angle (not shown) was approximately 0 degrees at resonance. In practice, the TCA was found to operate best when driven at 1.34 MHz with the portable ultrasound generator that was used in this study. Estimates of the acoustic output power and intensity from the Mason transmission line model at 1.34 MHz and the power and intensity measured with the hydrophone were within +/−10% of each other.

The stereotaxic guided TCA allowed for accurate insertion of the infusion cannula into the rat caudate and the portable ultrasound system freed up considerable bench-top space as compared to traditional bench-top RF amplifiers that require wall power. This allowed the experiment to be conducted in a straight forward and repeatable manner.

Ultrasound Dosimetry

The mechanical index (MI) is a standard measure of the acoustic output in ultrasound systems defined as the peak rarefactional pressure of an ultrasound longitudinal wave propagating in a uniform medium, divided by the square root of the center frequency of the transmitted ultrasound wave. According to the FDA for diagnostic obstetrics application, the MI should not exceed 1.9, and for ophthalmic applications the MI should not exceed 0.2 (AIUM. (1988). Bioeffects considerations for the safety of diagnostic ultrasound. *J Ultrasound Med.*, 7(9 Suppl), S1-S38; AIUM. (1993). *Bioeffects and safety of diagnostic ultrasound.* Laurel, Md.: American Institute of Ultrasound in Medicine; AIUM. (2000). *Mechanical bioeffects from diagnostic ultrasound: AIUM consensus statements,* 19, 67-170). To calculate the maximum MI achieved by the TCA using S.I. units (f=1.34 MHz, I=950 W/m$^2$), the intensity (I) and acoustic impedance of soft tissue (Z~1.6e6 kg/m$^2$s) was used (Schroeder, A. et al. (2009). Ultrasound, liposomes, and drug delivery: Principles for using ultrasound to control release of drugs from liposomes. *Chem. Phys. Lipids.* 162, 1-16) to calculate the pressure (P) and derived the following formula for the TCA to calculate a MI of 0.034 according to:

$$MI = \frac{P}{\sqrt{f}} = \frac{\sqrt{I \cdot Z}}{\sqrt{f}} = \frac{\sqrt{950 \cdot 1.6e6}}{\sqrt{1.34}} \times 10^{-6} = 0.034 \qquad (1)$$

Another standard measure is the thermal Index (TI). TI is defined as the ratio of the emitted acoustic power to the power required to raise the temperature of tissue by 1° C. The TI is intended to indicate the likely temperature rise that might be produced after long exposure. A larger TI value represents a higher risk of damage due to temperature increases. For therapeutic applications, the FDA requires that TI's over 6 require further explanation and safety analysis. The calculated soft-tissue thermal index ($T_s$) using the ultrasound power (P) for the TCA was 0.638 as calculated by:

$$T_s = \frac{P \cdot f}{210} = \frac{(0.11)(1.34e3)}{210} = 0.638 \quad (2)$$

The calculated MI was less than 0.2 and the $T_s$ value achieved was less than 6 for the TCA. The TCA is considered safe according to established FDA guidelines and standards developed from the American Institute of Ultrasound in Medicine.

In Vivo Ultrasound-Assisted Convection Enhanced Delivery

Typical raw data sets are presented in FIGS. 4A-D from the CED (4A), CED+MB (4B), UCED (4C) and UCED+MB (4D) subgroups of group 2 receiving 0.5 µL per min infusions. FIGS. 4A-D shows brain sections from the four subgroups of group 2 studied after 30 minutes of Evans blue infusions at 0.5 µL per minute with a 30 gauge cannula. Convection enhanced delivery (CED) (FIG. 4A) and convection enhanced delivery with microbubbles (CED+MB) (FIG. 4B) provide similar infusion profiles for the rodents in each group. Ultrasound-assisted convection enhanced delivery (UCED) (FIG. 4C) delivers EBD further into the brain and more diffusely spread across the caudate. Ultrasound-assisted convection enhanced delivery with microbubbles (UCED+MB) FIG. 4D) shows further EBD penetration over CED and CED+MB, but is more localized in the rodent caudate versus UCED which spreads EBD out of the caudate region. Backflow of EBD along the needle track into the white matter track of the corpus callosum is reduced with UCED and UCED+MB as compared to controls.

In FIGS. 4A-D, a dark border is shown around the brain section of the cannula insertion point in each of the four subgroups. In FIG. 4A, the cannula insertion point was in the section in the second row, second from the left. In FIG. 4B, the cannula insertion point was in the section in the second row, second from the left. In FIG. 4C, the cannula insertion point was in the section in the third row, third from the left. In FIG. 4D, the cannula insertion point was in the section in the fourth row, first on the left.

Image slices in each subgroup are 250 µm apart from one another in both anterior and posterior directions. The results illustrate EBD distribution volume in the rodent brain for 30 min of treatment. Optically quantifiable, EBD pigment is more diffuse and extends over a broader per slice area and total number of slices during UCED and UCED+MB as compared to CED and CED+MB. Backflow of EBD along the needle track into the corpus callosum during 0.5 µL per min infusions is also more pronounced in the CED and CED+MB subgroups as compared to the UCED and UCED+MB subgroups. In the slower 0.254, per min infusions (not shown) backflow as well as convection of EBD into the caudate region was reduced.

FIGS. 5A-D shows the three-dimensional reconstructions of EBD distribution volumes in the presented brain slices of FIGS. 4A-D for the left hemisphere and left caudate of the rodent brain, respectively. FIGS. 5A-D show the volume distribution of group 2 0.5 µL per min EBD infusions during CED, CED+MB, UCED and UCED+MB, respectively. In the CED and CED+MB controls (5A and B) the EBD dye stays in an 810×675×2500 µm volume around the infusion cannula in the gray matter of the caudate and the highly permeable white matter track of the corpus callosum. In UCED and UCED+MB treatment (5C and D), the EBD penetrates out of the control volume distribution by 2.24 to 3.25 and 1.16 to 1.70 times, respectively (p<0.001), and though the entire left caudate in the case of UCED radiating into the ventricles and corpus callosum of the rat brain.

MatLab analysis comparing the total distribution volume of EBD in the rodents' left hemisphere and left caudate for the two 0.25 and 0.5 µL per min infusion groups and respective subgroups is shown in FIG. 6. For each group in the bar graph, the first bar is CED, second bar is CED+MB, third bar is UCED and fourth bar is UCED+MB. ANOVA analysis between the subgroup means was statistically significant p<0.05 and p<0.001 with standard deviations of the CED, CED+MB, UCED and UCED+MB groups of 0.29, 1.50, 0.67 and 1.68, respectively in the left brain, 0.41, 1.95, 0.71 and 0.65, respectively in the left caudate for 0.25 µL per min infusion of group 1, and 1.90, 5.31, 0.56, 1.25, respectively in the left brain, 0.62, 1.99, 0.36, 0.40, respectively in the left caudate for 0.54 per min infusion of group 2. UCED and UCED+MB increased the distribution volume of EBD by 2.24× and 1.37× (46.3 mm$^3$ and 26.9 mm$^3$) as compared to CED and CED+MB (20.6 mm$^3$ and 19.7 mm$^3$) in the left hemisphere of the rodent brain in group 1, respectively. Within the left caudate of group 1, UCED and UCED+MB increase the distribution volume of EBD by 2.44× (33.1 mm$^3$) and 1.7× (27.0 mm$^3$) as compared with CED (13.6 mm$^3$) and CED+MB (15.9 mm$^3$), respectively. For the higher infusion rate of group 2, UCED and UCED+MB increase the distribution volume of EBD by 2.96× (111 mm$^3$) and 1.16× (37.1 mm$^3$) as compared to CED (37.4 mm$^3$) and CED+MB (31.9 mm$^3$) in the left hemisphere, and 3.25× (70.2 mm$^3$) and 1.54× (30.2 mm$^3$) in the left caudate, respectively.

FIGS. 7 and 8 represent the EBD distribution profile in the rodent caudate for subgroups of Group 1 and Group 2, respectively. FIGS. 7 and 8 show the area of EBD in the caudate of the rodent brain for each slice as a function of the anterior-posterior (AP) distance, defined here as the distance between the slice and the slice containing the infusion point. The black lines represent the area of slices averaged over all animals in each subgroup. The shaded regions represent the standard deviations of the data within each subgroup (n=5). Area measurements below 0.3 mm$^3$ in FIGS. 7 and 9 are subject to artifact from poor signal to noise ratio. Additionally, the TCA provided an acoustic field perpendicularly circumferential to the cannula, approximately 3.2 mm in radius at the infusion site. Across all groups and subgroups, the maximum area of penetration occurs in slices near the infusion point, and the penetration area decreases as the distance from the infusion sites increase in both directions. Ultrasound-assisted subgroups (UCED and UCED+MB) show greater distribution of EBD in the rodent caudate with a larger per slice area of EBD. Ultrasound-assisted subgroups also show higher standard deviations of EBD area in each slice as compared to CED alone. The area under each curve corresponds to the total volume distribution as presented in the bar graph of FIG. 6.

To obtain additional information about the shape of the distribution volume for the infusion protocols of Group 1 and Group 2, the data in FIGS. 7 and 8 were redrawn in FIG. 9 as a function of the square of the AP distance, i.e. the distance between the slice and slice containing the infusion point. If the infusion of EBD into the rodent caudate were isotropic and the shape of the EBD infusion volume was spherically symmetrical around the AP direction, then the control subgroups (CED and CED+MB) in FIG. 9 should fall on a straight line with slope of magnitude π (Neeves, K. B., et al. (2007). Dilation and degradation of the brain extracellular matrix enhances penetration of infused polymer. *Brain Res.*, 1180, 121-132), and the ultrasound-assisted subgroups (UCED and UCED+MB) could have a different distribution profile. The data for the CED, UCED, CED+MB and UCED+MB treatments in FIGS. 7 and 8 approximate straight lines with slopes close to π, but only in the vicinity of the infusion point. This suggests that the distribution volume is spherical for these groups close to the infusion point, but that it deviates from sphericity away from the infusion point. For UCED and UCED+MB subgroups, the magnitude of the slope decreases slower than it does for CED and CED+MB. The spherical part of the distribution is smallest for Group 2 CED, which has a spherical distribution only for the first five or six slices adjacent to the infusion point. For all of the data groups, the magnitude of the slope diminishes with increasing distance from the infusion point. This indicates preferential transport of EBD in the AP direction, i.e. orthogonal to the slices. Of all subgroups studied, ultrasound-assisted infusions maintain the largest distribution, particularly in the case of the higher infusion rate of Group 2. One might expect the UCED and UCED+MB distribution patterns to vary beyond the ultrasound field (circularly +/−3.2 mm perpendicular to cannula tip), however due to size limitations of the rodent brain and experimental setup this ultrasound field boundary effect is unnoticeable. Additionally, area measurements of EBD falling below (0.3 mm$^2$) may have image artifact and not enough contrast to obtain accurate signal to noise ratios. For reference, dotted line segments with slope of magnitude π are drawn in FIG. 9.

Gross examination of the brain was performed after ultrasound exposure to detect visible lesions on the brain surface. Visual examination of the post-UCED treated brains did not indicate any noticeable damage or significant change to the brain structure as compared with CED. The histological examination for the four groups is shown in FIG. 10. The histology shows CED, CED+MB, UCED and UCED+MB subgroups of Group 2 after H&E staining in the coronal plane. The arrow with box on the slides denotes the area of magnification and position of needle track. Histologic changes are similar across all groups and include mild parenchymal disruption, edema and hemorrhage around the needle track and injection site. In some cases, hemorrhage extends a short distance within the leptomeninges or along white matter tracts. Rare neurons directly associated with the needle tracks have pyknotic nuclei (necrosis). Also, in all groups, cortical neurons are multifocally basophilic and angular (dark neurons) and there are occasionally well-circumscribed foci of edema in the superficial cerebral cortex. These changes are not restricted to the injection site and are interpreted as artifacts of surgery and/or handling. Overall, histology for all groups show only minor acute damage since cells are distributed evenly and proper anatomical structure is maintained for the four groups.

6.1.5 Discussion

This example investigated whether a 1.34 MHz ultrasound transducer cannula device powered by a portable, light-weight ultrasound system could be used for ultrasound-assisted convection enhanced delivery to the brain in vivo. Sonicators of various forms have been shown to enhance transport transdermally in vitro and in vivo through the skin using low intensities (Mitragotri, S., et al. (1995). Ultrasound-mediated transdermal protein delivery. *Science*, 269, 850-853; Boucaud, A., et al. (2002). Effect of sonication parameters on transdermal delivery of insulin to hairless rats. *J. Pharm., Sci.* 91, 113-119; Machet, L., et al. (2002). Phonophoresis: efficiency, mechanisms and skin tolerance. *Int. J. Pharm.*, 243, 1-15; Smith, N. B., et al. (2003). Ultrasound-mediated transdermal in vivo transport of insulin with low-profile cymbal arrays. J. *Ultrasound Med. Bio.*, 29, 1205-1210), as well as various other tissues such as muscle and brain (Lewis, G. K., et al. (2007). A phantom feasibility study of acoustic enhanced drug perfusion in neurological tissue. *Proc. IEEE, LISA*, 67-70; Lewis, Jr. G. K., et al. (2007). Acoustic targeted chemotherapy in neurological tissue. *J. Acoust. Soc. Am.*, 122, 3007; Lewis Jr., et al. (2008). Therapeutic ultrasound enhancement of drug delivery to soft tissues. 8*th. Int. Sym. Ther. Ultrasound, AIP conf Proc.*, 1113, 403-407).

Considerable amounts of research have been conducted in using pulsed high intensity focused ultrasound (HIFU) to open the blood brain barrier and allow systemically administered therapy to enter the brain, and HIFU shows great promise as a new technique to deliver targeted therapy (Patrick, J. T., et al. (1990). Ultrasound and the blood brain barrier. *Adv. Exp. Med. Biol.*, 267, 369-381; Hynynen, K., et al. (2007). Clinical applications of focused ultrasound—The brain. *Int. J. Hyperth.*, 23, 193-202). Convection enhanced delivery (CED) techniques for drug delivery to the brain have also made major strides over the last 10 years. The maximum flow rate and therapeutic penetration of drug that can be achieved in CED, however, is known in the art to be often determined by the onset of backflow along the outside of the infusion cannula. Backflow along the tissue cannula interface is directly proportional to the volumetric flow rate imposed, the radius of the infusion cannula and the permeability/tissue-resistance to convective transport.

The transducer cannula assembly (TCA) and portable ultrasound system used in this study was utilized to simultaneously sonicate and inject Evan's blue dye (EBD) into the caudate of the rat brain. The application of 1.34 MHz at a total acoustic power of 0.11+/−0.005 W and peak spatial intensity at the cannula tip of I=0.0497 W/cm$^2$ was shown to enhance the volume distribution of EBD into the caudate of the rat by 2.44× and 3.25× at 0.25 μL/min and 0.5 μL/min infusion rates, respectively as compared to the controls (p<0.001). Gross and histological examination showed no significant cellular damage to the rat brain due to ultrasound exposure.

As shown in FIG. 6, where the volume distribution was calculated for the eight subgroups, ultrasound had an overall effect of increasing EBD distribution in the brain tissue by approximately 2.24 to 3.25× for UCED, and 1.16 to 1.70× for UCED+MB subgroups as compared with controls. This is visualized in FIGS. 4C and 4D and reconstructed in FIGS. 5C and 5D, where UCED provided extended EBD distribution. FIGS. 7, 8 and 9 also show that ultrasound-assisted infusions increase the per slice area of EBD penetration. Ultrasound may provide a mechanism here to mitigate EBD vascular clearance and elimination from the brain, which presents one of the challenges for CED as discussed above.

The effect of increased volumetric distribution in the caudate with stabilized microbubbles measured in the UCED+MB infusions of Groups 1 and 2 as compared with CED+MB controls may have resulted from increased streaming (Sakamoto, S., et al. (1999). Effects of existence of microbubbles for increase of acoustic streaming. *Jpn. J. Appl. Phys.,* 38, 3050-3052; Collis, J., et al. (2010). Cavitation microstreaming and stress fields created by microbubbles. *Ultrasonics,* 50, 273-279) and micro-mixing (Collis, J., et al. (2010). Cavitation microstreaming and stress fields created by microbubbles. *Ultrasonics,* 50, 273-279; Farrara, K., et al. (2007). Ultrasound microbubble contrast agents: Fundamentals and application to gene and drug delivery. *Annual. Rev. Biomed. Eng.* 9, 415-447) of the microbubbles and EBD at the needle/tissue interface. However, an overall reduction of volumetric distribution of EBD was found with the addition of microbubbles into the infusate when compared with UCED alone. The microbubbles possibly acted as acoustic absorbers and reflectors in the brain parenchyma, thereby limiting the ultrasound effect to a smaller region of the brain by attenuating ultrasound beyond the infusion volume. The mixing and oscillation of the microbubbles in the acoustic field may have had an effect of improving EBD delivery into the caudate brain tissue over CED+MB subgroups. The propagation of the microbubbles in the direction of the acoustic radiation generated characteristic elliptical infusion profiles in the UCED+MB subgroups with the long access of the ellipse being parallel to the infusion cannula. Interestingly, CED and CED+MB infusions have approximately the same total distribution volume in the caudate as shown in FIG. 6 but have different caudate infusion profiles as shown in FIGS. 7 and 8. CED+MB infusions have higher EBD distribution close to the infusion point versus CED infusions.

Ultrasound-assisted convection enhanced delivery (UCED) shows advantages over traditional CED in the rat brain and warrants further investigation into the mechanisms of augmentation. The interaction of the ultrasound field on brain tissue permeability during UCED treatment should be assessed and probed real-time under parametric sonication intensities. During CED infusions, the pressure at the outlet of the needle is sufficiently large to deform the tissue radially, forming a fluid-filled cavity around the needle tip. The interaction of ultrasound with this cavity/tissue interface could enhance mass transfer from the cavity into the tissue. Frenkel et al. showed that non-destructive low intensity ultrasound widened intercellular spaces between epithelial cells at fluid-tissue interfaces (Frenkel, V., et al. (2006). Pulsed-high intensity ultrasound (HIFU) enhances thrombolysis in an in vitro model. *Radiol.,* 239, 86-93). Investigations into the phenomenon indicated that the effects were due to transverse waves generated at the fluid/tissue interface. These waves increased the penetration and mass transport of nanoparticles from the fluid medium into adjacent epithelium, and increased the rate of effective diffusion through the tissues (Frenkel, V., et a. (2000). Ultrasound-facilitated transport of silver chloride (AgCl) particles in fish skin. *J Cont. Release,* 68, 251-261).

Acoustic streaming has been shown to increase the mass transport of nanoparticles for improved transdermal delivery (Frenkel, V., et al. (2000). Ultrasound-facilitated transport of silver chloride (AgCl) particles in fish skin. *J. Cont. Release,* 68, 251-261; Ohl, C. D., et al. (2006). Sonoporation from jetting cavitation bubbles. *Biophys J.,* 91, 4285-4295; van Wamel, A., et al. (2006). Vibrating microbubbles poking individual cells: drug transfer into cells via sonoporation. *J. Cont. Release,* 112, 149-155). The imposed radiation force on infusate shows promise to mitigate and prevent backflow along the tissue/cannula interface thereby allowing greater infusion rates in CED. At the higher infusion rate of Group 2, CED subgroups showed backflow and reduction of EBD delivery to the caudate whereas UCED subgroups were able to successfully deliver at higher infusion rates into the rodents caudate. However due to the small size of the rodent caudate, during UCED protocols EBD radiated into the ventricles of the rodent brain.

Additionally, acoustic cavitation is currently considered to be one of the most dominant and vital mechanism for ultrasound mediated drug delivery (Patrick, J. T., et al., (1990). Ultrasound and the blood brain barrier. *Adv. Exp. Med. Biol.,* 267, 369-381; Hynynen, K., et al. (2007). Clinical applications of focused ultrasound—The brain. *Int. J. Hyperth.,* 23, 193-202; van Wamel, A., et al. (2006). Vibrating microbubbles poking individual cells: drug transfer into cells via sonoporation. *J. Cont. Release,* 112, 149-155). Numerous in vivo studies have shown that stabilized microbubbles, used as cavitational nucleation agents, make ultrasound mediated delivery more efficient, useful, and able to be conducted under low acoustic intensities. In some applications, microbubbles are shown to enable ultrasound mediated delivery where low-intensity ultrasound alone was ineffective (Ohl, C. D., et al. (2006). Sonoporation from jetting cavitation bubbles. *Biophys J.,* 91, 4285-4295; van Wamel, A., et al. (2006). Vibrating microbubbles poking individual cells: drug transfer into cells via sonoporation. *J. Cont. Release,* 112, 149-155).

In this example, microbubbles at the concentration and acoustic intensity applied hindered improving the distribution volume of EBD. However, microbubbles may be useful in improving UCED at different acoustic intensities and pulse sequences, and at lower microbubble infusate concentrations. In addition to microbubbles, larger molecular weight infusate molecules and nanoparticles that present a greater challenge to CED in clinical practice can be used with UCED administration in vivo. Finally, CED catheter designs known in the art can be employed in the TCA.

6.1.6 Conclusion

Ultrasound continues to evolve with new uses in a range of medical applications from drug delivery to non-invasive surgical techniques. With the price of portable and powerful ultrasound therapy equipment decreasing and the uses of ultrasound in medicine increasing, many more ultrasound assisted modalities are in the pipeline for treatment of human diseases. In particular, treatment of malignant brain tumors, which pose particular challenges due to the obstacles known to limit drug delivery in the brain. This example shows that ultrasound is capable of safely enhancing the permeation and distribution of small molecules through the rat caudate in vivo. These in vivo findings show that ultrasound energy interactions with tissues and fluids can have a broad impact to improve CED treatments in human patients; not only with the present embodiment of the ultrasound TCA device, but potentially with any CED cannula design known in the art.

6.2 Example 2: In Vivo Ultrasound Assisted Convection Enhanced Delivery: Power Ranging Analysis and Standing Wave Phenomena 6.2.1 Introduction Therapeutic ultrasound has been used to enhance and/or mediate drug delivery in various applications including convection-enhanced delivery (CED) of tracers to the rodent brain. While ultrasound has been shown to increase the delivery volume of tracers in neurological tissue safely, the exposure range of safe ultrasound energy levels is not well documented and/or explored. This is especially true in the case of continuous low-intensity ultrasound therapy to the brain as discussed in Section 6.1, Example 1, since most research has focused on using ultrasound to disrupt the blood-brain barrier at much higher acoustic intensities but for much shorter ultrasonic application times. In the present example, to explore the acute effects of ultrasound to the live rodent brain, ultrasound was applied using the Transducer Cannula Assembly (TCA) through a small craniotomy in vivo under four different acoustic intensities ranging from 0.062 to 0.155 W/cm$^2$ in a total of 4 Sprague-Dawley rats for 30 minutes. Histological analysis was then conducted on the brain tissue specimens to assess for neuronal damage.

Additionally, because ultrasound is being used in continuous wave mode for ultrasound-assisted CED (UCED), standing waves can be induced in the brain tissue and generate banding patters of tracers. The example demonstrates the results of this observed "standing wave phenomena" in the rodent brain in vivo during UCED, which shows that low-intensity ultrasound may provide a tool for additional drug delivery applications beyond improving the distribution of pharmaceuticals in the brain.

6.2.2 Introduction to Standing Waves

Standing waves are well documented phenomena formed by the constructive interference of two mechanical waves traveling in opposite directions, including ultrasound waves propagating in a media. The constructive interference of two equal and opposite waves, and the formation of a standing wave results in an interference pattern with nodes and anti-nodes that do not move in space temporally. The anti-nodes represent the maximum displacement and amplitude of the ultrasound wave, whereas the nodes represent areas of minimum displacement which experience very little acoustic pressure from the ultrasound wave. Standing waves are commonly formed when an ultrasound source of consistent frequency and position, continuously generates an incident wave which then interferes with its own reflection off a boundary.

Standing waves have been exploited in a number of applications, both biomedical and otherwise. Some examples include using ultrasonic standing waves to immobilize cells in a gel matrix at areas of minimal acoustic pressure (nodes) in the standing wave field as well as creating a physical force field filter within microfluidic devices (Gherardini, L., et al. (2005). A new immobilization method to arrange particles in a gel matrix by ultrasound standing waves. *Ultrasound in Med. & Biol.* 31, 261-2721 Hawkes, J. J., et al (2001). Force field particle filter, combining ultrasound standing waves and laminar flow. *Sensors and Actuators B* 75, 213-222). However, it is generally believed that standing waves in brain tissue are undesirable since localized high energy sites at the anti-nodes could cause damage to neuronal tissue. At the 1-2 MHz frequencies in particular, the wavelength resembles the dimension of an artery in the brain, which could prove problematic if high energy spots were formed on this scale (Culp, W. C, McCowan, T. C. (2005). Ultrasound augmented thrombolysis. *Current Medical Imaging Reviews* 1, 5-12).

6.2.3 Materials and Methods

Ultrasound Generator and Ultrasound Exposimetry

An art-known ultrasound generator, the ultrasound generator disclosed in Lewis and Olbricht (WO2010/006293A9, entitled Ultrasound Wave Generating Apparatus, PCT/US2009/050297) was powered with two adjustable 0-20 V standard lab power supplies to drive the Transducer Cannula Assembly (TCA) discussed in Section 6.1, Example 1, up to the maximum +/−20 V power setting. The acoustic power and intensity was measured using a calibrated hydrophone and power meter as in Example 1. The four acoustic intensities at the cannula tip and total acoustic powers applied to the rodent brains during UCED were 0.062 W/cm$^2$ and 0.12 W+/−0.005 W, 0.087 W/cm$^2$ and 0.16 W+/−0.005 W, 0.112 W/cm$^2$ and 0.23 W+/−0.005 W, and 0.155 W/cm$^2$ and 0.31 W+/−0.005 W.

Power Ranging Animal Experiments

Rats were anesthetized and euthanized by procedures approved by the Institutional Animal Care and Use Committee (IACUC) at Cornell University. A total of 4 Sprague-Dawley rats (350 to 450 g) received UCED at 4 different ultrasound intensities ranging from 0.062 to 0.155 W/cm$^2$ for 30 min. A small craniotomy was made as in Chapter 9 to expose the brain. The TCA was guided using a micromanipulator to +0 mm anterior, +3 mm lateral and −5.5 mm ventral from bregma, lowered at 0.25 mm per second into the caudate of the rat brain and allowed to equilibrate for two minutes. 1-2 ml of artificial cerebral spinal fluid (aCSF) and a gel-foam dam was used to couple acoustic energy from the face of the TCA into the rodent brain. The TCA was powered on with the ultrasound generator.

Filtered Evan's blue dye (EBD) 0.25 wt % in phosphate buffered saline (PBS) was infused using a microinfusion pump with a starting infusion flow rate of 0.1 μL/min for 5 min, the infusion flow rate was then increased to 0.25 μL/min for an additional 5 min, to the final flow rate of 0.5 μL/min for 20 min. After 30 min of simultaneous infusion and ultrasound therapy the experiment was stopped. The TCA was left in the tissue for 1-2 min before being removed while euthanasia via cardiac urethane injection was performed. The rodent brains were prepared for histological analysis and reviewed by the Veterinary Pathology Department at Cornell University as in Example 1.

6.2.4 Histological Results and Conclusions from Power Ranging

Gross examination of the brain was performed after ultrasound exposure to detect visible lesions on the brain surface. Visual examination of the post-UCED treated brains did not indicate any noticeable damage or significant change to the brain structure. The histological examination for the four groups is shown in FIG. 11. The arrow with box on the slides denotes the area of magnification and position of needle track. Histologic changes are similar across all groups as well as rodents receiving lower acoustic UCED intensities as discussed in Example 1. Histology showed mild parenchymal disruption, edema and hemorrhage around the needle track and injection site. In some cases, hemorrhage extended a short distance within the leptomeninges or along white matter tracts. Rare neurons directly associated with the needle tracks show pyknotic nuclei (necrosis). Also, in all groups presented, cortical neurons are multifocally basophilic and angular (dark neurons) and there are occasionally well-circumscribed foci of edema in the superficial cerebral cortex. These changes were not restricted to the injection site and are interpreted as artifacts of surgery and/or handling.

The results presented here show that ultrasound applied below 0.155 W/cm$^2$ to the brain for 30 min produced no noticeable neuronal damage to the caudate or cortex. Further determination of the level of ultrasound exposure to the brain that causes acute neuronal damage can be determined using the methods described hereinabove. Art known methods of parametric analysis can also be used to understand the safe operating window for UCED. Routine acute exposure and histology studies can also be employed to assess neurological damage from ultrasound exposure since neuronal degeneration may take up to 3-5 days before detectable by cresyl violet staining (Bancroft, J. D., Gamble, M. (2008). Theory and practice of histological techniques, Sixth Edition. Elsevier, Philadelphia Pa. pp. 366-388).

6.2.5 Standing Wave Findings and Discussion

In vivo brain drug delivery using 1.34 MHz ultrasound in conjunction with CED was employed to infuse Evans blue dye directly into the rat brain caudate. The results are generally a distribution volume of dye with a spherical or ellipsoid shape as shown in FIG. 12A. However, in two rodents during the vast UCED experimentation, distinct, non-continuous bands of dye were observed in brain sections close to the needle track and directly above the TCA as shown in FIG. 12B. This phenomenon could be attributed to the formation of a standing ultrasound wave within the rat brain during the UCED infusion. This formation is likely the result of the incident ultrasound waves interfering with reflections from the rodent skull generating a steady spatial field of nodes and anti-nodes.

The observed banding is analogous to other processes whereby material accumulates in a standing wave field. However, the exact mechanism in brain tissue has not yet been identified. One possibility is that the tracer accumulates in the nodes, or the areas of least acoustic pressure. The other possibility is that the tracer accumulates at the anti-nodes where the ultrasound waves have the greatest amplitude. This increased energy could cause increased tissue permeability, causing tracer to preferentially accumulate at the anti-nodes.

To better understand whether tracer is accumulating at the nodes or anti-nodes the wavelength of ultrasound in brain tissue was calculated. The result was compared to the distance between the bands, $$f = \frac{c}{\lambda} \quad (3)$$

where f is the frequency, c is the speed of sound in brain tissue (1460 m/s, Goss S A, et al. (1980). Compilation of empirical ultrasonic properties of mammalian tissues. *J Acoust. Soc Am.* 68 (1980), 93-108), and $\lambda$ is the wavelength. The wavelength was calculated to be 1.09 mm, resulting in a node to node distance of 0.545 mm. The distance between the bands in the two experiments experiencing this phenomena are approximately 0.6 mm, which supports the conclusion that dye is accumulating at the nodes.

Though this result runs counter to the objective of maximizing volume distribution of an infusate as discussed in Example 1, it may have other applications. For instance, if various standing wave patterns could be induced during an infusion, greater spatial and temporal control over the infusion could be achieved; this control could prove especially valuable with highly toxic treatments. Difficulty arises in reproducing this in vivo result. Inducing a standing wave depends on correct alignment in the desired geometry as well as the correct ultrasound frequency. Inducing such a standing wave field in vivo would likely require real-time imaging and precise positioning of the ultrasound source. However, if standing waves prove harmful to the brain, measures can be taken to prevent their formation, such as randomizing frequency or moving the source (Tang, S. C., et al. (2010) Standing wave suppression for transracial ultrasound by random modulation. *IEEE Trans Biomed Eng.* 57 203-5).

This observation of standing waves shows that ultrasound is not only having an effect on brain tissue, but that ultrasound also directly affects the distribution profile of the infusate during CED. Thus this example advances the knowledge of how ultrasound can affect the infusion profile, which in turn allows for the parameters governing UCED to be optimized, using standard methods known in the art, as UCED evolves into a clinically relevant therapy for neurological and other disorders.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. An ultrasound transducer cannula assembly (TCA) apparatus comprising:
    a cannula;
    an ultrasound transducer;
    an ultrasound driver wherein the ultrasound driver produces an ultrasound drive signal waveform; and
    a connection between the ultrasound driver and the ultrasound transducer;
    wherein the apparatus is operative for monitoring acoustic energy produced by the ultrasound transducer, and wherein the apparatus is further operative for one or more of the following consisting of (a) adjusting power produced by the ultrasound transducer, and (b) modulating the ultrasound drive signal waveform; and
    wherein activation of the ultrasound transducer creates an acoustic field that is one or more of around, within or through the cannula, wherein the apparatus includes a lens associated to the ultrasound transducer to focus acoustic energy produced by the ultrasound transducer.

2. The apparatus of claim 1, wherein the cannula comprises the ultrasound transducer.

3. The apparatus of claim 1, comprising a second cannula for guiding the cannula (hereinafter "guide cannula").

4. The apparatus of claim 1, wherein the ultrasound transducer comprises portions defining a hole, canal or groove for positioning of the cannula.

5. The apparatus of claim 4, wherein the ultrasound transducer comprises portions defining a plurality of holes, canals or grooves for positioning of a plurality of cannulas.

6. The apparatus of claim 1, comprising a stereotaxic, manual or robotic guide arm.

7. The apparatus of claim 1, comprising a plurality of ultrasound transducers, wherein a member of the plurality of ultrasound transducers produces a different frequency of ultrasound from another member of the plurality of ultrasound transducers.

8. The apparatus of claim 1, comprising a plurality of ultrasound transducers, wherein the frequency produced by one member of the plurality of ultrasound transducers and the frequency produced by another member of the plurality of ultrasound transducers have different bioacoustical qualities.

9. The apparatus of claim 1, wherein the apparatus produces a standing wave or acoustic field.

10. The apparatus of claim 1, wherein the cannula includes the ultrasound transducer disposed outside the cannula.

11. The apparatus of claim 1, wherein the cannula includes the ultrasound transducer disposed inside the cannula.

12. The apparatus of claim 1, wherein the ultrasound transducer is an elongated ultrasound transducer and wherein the cannula includes the ultrasound transducer disposed on the cannula so that the ultrasound transducer is coextensive with the cannula.

13. The apparatus of claim 1, wherein the cannula includes a plurality of ultrasound transducers spaced apart along a length of the cannula.

14. The apparatus of claim 1, wherein the apparatus is operative for each of (a) adjusting power produced by the ultrasound transducer, and (b) modulating the ultrasound drive signal waveform.

15. The apparatus of claim 1, wherein the lens associated to the ultrasound transducer is shaped to focus acoustic energy produced by the ultrasound transducer to produce an acoustic field of a desired arbitrary shape.

16. The apparatus of claim 1, wherein the lens associated to the ultrasound transducer is shaped to focus acoustic energy produced by the ultrasound transducer to produce an acoustic field of a desired shape, the desired shape being a desired pattern of compound(s) that are infused to target cells, tissues or organs.

17. The apparatus of claim 1, and wherein the apparatus is further operative for one or more of the following selected from the group consisting of (a) adjusting power produced by the ultrasound transducer, and (b) modulating the ultrasound drive signal waveform.

18. The apparatus of claim 1 wherein the apparatus is operative to monitor a Mechanical Index (MI) of the apparatus during use of the apparatus to direct ultrasound energy to body tissue.

19. The apparatus of claim 1, wherein the apparatus is operative to monitor a thermal index (TI) of the apparatus during use of the apparatus to direct ultrasound energy to body tissue, the thermal index (TI) indicating a predicted temperature rise of the body tissue attributable to a directing the ultrasound energy to the body tissue.

20. A method for ultrasound-assisted convection-enhanced delivery (UCED) of a compound to a targeted cell, tissue, organ or region of the body (hereinafter "target") in a subject comprising the steps of:
providing an ultrasound transducer cannula assembly (TCA) apparatus having a cannula and an ultrasound transducer; wherein activation of the ultrasound transducer creates an acoustic field around that is one or more of around, within or through the cannula;
contacting the ultrasound TCA apparatus to the target;
introducing the compound (or a solution thereof) into cannula;
activating the ultrasound transducer, thereby producing an acoustic field; and
releasing the compound from the cannula, whereby the compound contacts the target wherein the step of activating the ultrasound transducer is before the step of releasing the compound, wherein the method includes contacting the ultrasound TCA apparatus to the target and wherein the step of activating includes performing the activating before the contacting the TCA apparatus to the target while the ultrasound TCA apparatus is being guided to the target so that the cannula is vibrating while the ultrasound TCA apparatus is being guided to the target and while the contacting the ultrasound TCA apparatus is being performed.

21. The method of claim 20, wherein the contacting step comprises stereotactically, manually or robotically guiding the ultrasound TCA apparatus to the target.

22. The method of claim 20, wherein the introducing step comprises adding stabilized microbubbles to the compound.

23. The method of claim 20, wherein the step of activating the ultrasound transducer produces a standing waveform or focused field.

24. The method of claim 20, wherein the step of activating includes performing the activating while the ultrasound TCA apparatus is being guided to the target so that the cannula is vibrating while the ultrasound TCA apparatus is being guided to the target.

25. A method comprising:
providing an ultrasound transducer cannula assembly (TCA) apparatus having a cannula; and a plurality of ultrasound transducers; wherein activation of an ultrasound transducer of the plurality of ultrasound transducers creates an acoustic field that is one or more of around, within or through the cannula, wherein a member of the plurality of ultrasound transducers produces a different frequency of ultrasound from another member of the plurality of ultrasound transducers;
activating a first ultrasound transducer of the plurality of transducers at a first frequency to permeabilize a cell or tissue; and
activating a second ultrasound transducer of the plurality of transducers at a second frequency to push or propel a compound to a desired target.

26. The method of claim 25, wherein the cannula assembly (TCA) apparatus included a plurality of cannulas, and wherein ultrasound transducers of the plurality of ultrasound transducers are distributed among cannulas of the plurality of cannulas.

27. The method of claim 25, wherein the method includes permeabilizing the cell or tissue, wherein the permeabilizing the cell or tissue includes activating the first ultrasound transducer of the plurality of transducers at the first frequency.

28. The method of claim 25, wherein the method includes pushing or propelling the compound to the desired target, wherein the pushing or propelling the compound to the desired target includes activating the second ultrasound transducer of the plurality of transducers at the second frequency.

29. A method for ultrasound-assisted convection-enhanced delivery (UCED) of a compound to a targeted cell, tissue, organ or region of the body (hereinafter "target") in a subject comprising the steps of:
providing an ultrasound transducer cannula assembly (TCA) apparatus having a cannula and an ultrasound transducer; wherein activation of the ultrasound transducer creates an acoustic field that is one or more of around, within or through the cannula;
contacting the ultrasound TCA apparatus to the target;
introducing the compound (or a solution thereof) into cannula;
activating the ultrasound transducer, thereby producing an acoustic field; and
releasing the compound from the cannula, whereby the compound contacts the target, wherein the step of activating the ultrasound transducer produces a standing waveform or focused field, wherein the step of activating the ultrasound transducer produces the standing waveform, and wherein the method includes generating a steady spatial field of nodes and anti-nodes within the target.

30. The method of claim 29, wherein the step of activating the ultrasound transducer produces the standing waveform or focused field to generate a desired pattern of the compound infused to target cells, tissues or organs.

31. The method of claim 29, wherein the step of activating the ultrasound transducer produces the standing waveform or focused field to confine the compound to a desired location in the tissue or organ.

32. The method of claim 29, wherein the method includes using acoustic pressure to prevent diffusion of the compound past a desired location.

33. The method of claim 29, wherein the step of activating the ultrasound transducer produces the standing waveform, and wherein the method includes using real-time imaging for aligning of the ultrasound TCA apparatus.

34. The method of claim 29, wherein the step of activating the ultrasound transducer produces the standing waveform, and wherein the method includes selecting a frequency and position for operating the ultrasound TCA apparatus.

35. The method of claim 29, wherein the step of activating the ultrasound transducer produces the standing waveform, and wherein the method includes using real-time imaging for aligning of the ultrasound TCA apparatus, and selecting a frequency and position for operating the ultrasound TCA apparatus.

36. The method of claim 29, wherein method includes using the TCA apparatus to produce the standing waveform in the targeted cell, tissue, or organ so that the standing waveform generates a desired pattern of the compound infused to the targeted cell, tissue or organ.

37. The method of claim 29, wherein method includes using the TCA apparatus to produce the standing waveform in the targeted cell tissue or organ so that the standing waveform confines the compound to a desired location in the targeted cell, tissue or organ.

38. The method of claim 29, wherein a compound has a desired location in the tissue or organ, wherein the method includes confining the compound to the desired location in the tissue or organ, wherein the confining includes activating the ultrasound transducer to produce a standing waveform or focused field.

39. The method of claim 29, wherein the method includes preventing diffusion of the compound past a specified location using acoustic pressure produced by the TCA apparatus.

40. The method of claim 29, wherein the method includes, to infuse the compound into the target, inducing a first standing waveform in the target using the TCA apparatus, and inducing a second standing waveform in the target using the TCA apparatus, the second standing waveform being different than the first standing waveform.

41. An ultrasound transducer cannula assembly (TCA) apparatus comprising:
a cannula; and
an ultrasound transducer;
an ultrasound driver wherein the ultrasound driver produces an ultrasound drive signal waveform;
a connection between the ultrasound driver and the ultrasound transducer;
wherein the apparatus is operative for monitoring acoustic energy produced by the ultrasound transducer, and wherein the apparatus is further operative for one or more of the following consisting of (a) adjusting power produced by the ultrasound transducer, and (b) modulating the ultrasound drive signal waveform; and
wherein activation of the ultrasound transducer creates an acoustic field that is one or more of around, within or through the cannula, wherein the apparatus is operative to monitor a Mechanical Index (MI) of the apparatus during use of the apparatus to direct ultrasound energy to body tissue.

42. An ultrasound transducer cannula assembly (TCA) apparatus comprising:
a cannula; and
an ultrasound transducer;
an ultrasound driver wherein the ultrasound driver produces an ultrasound drive signal waveform;
a connection between the ultrasound driver and the ultrasound transducer;
wherein the apparatus is operative for monitoring acoustic energy produced by the ultrasound transducer, and wherein the apparatus is further operative for one or more of the following consisting of (a) adjusting power produced by the ultrasound transducer, and (b) modulating the ultrasound drive signal waveform; and
wherein activation of the ultrasound transducer creates an acoustic field that is one or more of around, within or through the cannula, wherein the apparatus is operative to monitor a thermal index (TI) of the apparatus during use of the apparatus to direct ultrasound energy to body tissue, the thermal index (TI) indicating a predicted temperature rise of the body tissue attributable to the directing the ultrasound energy to the body tissue.

43. A method for ultrasound-assisted convection-enhanced delivery (UCED) of a compound to a targeted cell, tissue, organ or region of the body (hereinafter "target") in a subject comprising the steps of:
providing an ultrasound transducer cannula assembly (TCA) apparatus having a cannula and an ultrasound transducer;
wherein activation of the ultrasound transducer creates an acoustic field that is one or more of around, within or through the cannula;
contacting the ultrasound TCA apparatus to the target;
introducing the compound (or a solution thereof) into cannula;
activating the ultrasound transducer, thereby producing an acoustic field; and
releasing the compound from the cannula, whereby the compound contacts the target, wherein the step of activating the ultrasound transducer produces a standing waveform or focused field, wherein method includes using the TCA apparatus to produce the standing waveform in the targeted cell tissue or organ so that the standing waveform confines the compound to a desired location in the targeted cell, tissue or organ.

44. The method of claim 43, wherein the step of activating the ultrasound transducer produces the focused field, and wherein the method includes controlling a focus of the TCA apparatus to control infusion of the compound to the target.

45. A method for ultrasound-assisted convection-enhanced delivery (UCED) of a compound to a targeted cell, tissue, organ or region of the body (hereinafter "target") in a subject comprising the steps of:
providing an ultrasound transducer cannula assembly (TCA) apparatus having a cannula and an ultrasound transducer;
wherein activation of the ultrasound transducer creates an acoustic field that is one or more of around, within or through the cannula;

contacting the ultrasound TCA apparatus to the target;

introducing the compound, or a solution of the compound, into cannula;

activating the ultrasound transducer, thereby producing an acoustic field; and releasing the compound from the cannula, whereby the compound contacts the target, wherein the step of activating the ultrasound transducer produces a standing waveform or focused field, wherein a compound has a desired location in the tissue or organ, wherein the method includes confining the compound to the desired location in the tissue or organ, wherein the confining includes activating the ultrasound transducer to produce a standing waveform or focused field.

46. A method for ultrasound-assisted convection-enhanced delivery (UCED) of a compound to a targeted cell, tissue, organ or region of the body (hereinafter "target") in a subject comprising the steps of:

providing an ultrasound transducer cannula assembly (TCA) apparatus having a cannula and an ultrasound transducer;

wherein activation of the ultrasound transducer creates an acoustic field that is one or more of around, within or through the cannula;

contacting the ultrasound TCA apparatus to the target;

introducing the compound (or a solution thereof) into cannula;

activating the ultrasound transducer, thereby producing an acoustic field; and releasing the compound from the cannula, whereby the compound contacts the target, wherein the step of activating the ultrasound transducer produces a standing waveform or focused field, wherein the method includes, to infuse the compound into the target, inducing a first standing waveform in the target using the TCA apparatus, and inducing a second standing waveform in the target using the TCA apparatus, the second standing waveform being different than the first standing waveform.

* * * * *

UNITED STATES PATENT AND TRADEMARK OFFICE
CERTIFICATE OF CORRECTION

PATENT NO. : 10,537,725 B2
APPLICATION NO. : 13/582663
DATED : January 21, 2020
INVENTOR(S) : Lewis, Jr. et al.

Page 1 of 1

It is certified that error appears in the above-identified patent and that said Letters Patent is hereby corrected as shown below:

In the Claims

Column 37, Line 56: Claim 20, Delete "introducing the compound (or a solution thereof) into cannula;" and insert -- introducing the compound, or a solution of the compound, into cannula; --

Column 38, Line 60: Claim 29, Delete "introducing the compound (or a solution thereof) into cannula;" and insert -- introducing the compound, or a solution of the compound, into cannula; --

Column 39, Line 24: Claim 34, Delete "selecting a frequency" and insert -- selecting a constant operating frequency --

Column 40, Line 29: Claim 42, Delete "attributable to the" and insert -- attributable to a --

Column 40, Line 42: Claim 43, Delete "introducing the compound (or a solution thereof) into cannula;" and insert -- introducing the compound, or a solution of the compound, into cannula; --

Signed and Sealed this
Seventeenth Day of March, 2020

Andrei Iancu
*Director of the United States Patent and Trademark Office*